United States Patent
Minvielle

(10) Patent No.: US 10,219,531 B2
(45) Date of Patent: Mar. 5, 2019

(54) PRESERVATION SYSTEM FOR NUTRITIONAL SUBSTANCES

(75) Inventor: Eugenio Minvielle, Rye, NY (US)

(73) Assignee: Iceberg Luxembourg S.A.R.L., Luxembourg (LU)

( * ) Notice: Subject to any disclaimer, the term of this patent is extended or adjusted under 35 U.S.C. 154(b) by 362 days.

(21) Appl. No.: 13/485,854

(22) Filed: May 31, 2012

(65) Prior Publication Data
US 2013/0269542 A1   Oct. 17, 2013

Related U.S. Application Data

(60) Provisional application No. 61/624,948, filed on Apr. 16, 2012, provisional application No. 61/624,972, filed on Apr. 16, 2012, provisional application No. 61/624,985, filed on Apr. 16, 2012.

(51) Int. Cl.
*A23L 3/00* (2006.01)
*G01N 33/02* (2006.01)

(52) U.S. Cl.
CPC ............... *A23L 3/00* (2013.01); *G01N 33/02* (2013.01)

(58) Field of Classification Search
CPC .................................. G01N 33/02; A23L 3/00
USPC .................. 99/453–455, 467–476, 485–486; 73/865.8
See application file for complete search history.

(56) References Cited

U.S. PATENT DOCUMENTS 3,685,308 A   8/1972   Lundquist
4,225,410 A   9/1980   Pace
4,364,234 A   12/1982  Reed
4,555,930 A   12/1985  Leach et al.
4,644,137 A   2/1987   Asahi et al.
(Continued)

FOREIGN PATENT DOCUMENTS

CN   101173316        5/2008
CN   102033043 A      4/2011
(Continued)

OTHER PUBLICATIONS

Bell, S. et al., "Report on nutrient losses and gains factors used in European food composition databases", Technical Report, Apr. 2006, 66 pages (Retrieved from the Internet on Mar. 2, 2015 at: http://www/.eurofir.net).

(Continued)

*Primary Examiner* — Reginald Alexander
(74) *Attorney, Agent, or Firm* — Nixon Peabody LLP

(57) ABSTRACT

Disclosed herein is preservation system for nutritional substances. The preservation system obtains information about the nutritional substance to be preserved, senses and measures the external environment to the preservation system, senses and measures the internal environment to the preservation system, senses and measures the state of the nutritional substance, and stores such information throughout the period of preservation. Using this accumulated information, the preservation system can measure, or estimate, changes in nutritional content (usually degradation) during the period of preservation. Additionally, the preservation system can use this information to dynamically modify the preservation system to minimize detrimental changes to the nutritional content of the nutritional substance, and in some cases actually improve the nutritional substance attributes.

3 Claims, 13 Drawing Sheets

(56) References Cited

U.S. PATENT DOCUMENTS

| | | |
|---|---|---|
| 4,644,154 A | 2/1987 | Brogardh et al. |
| 4,650,766 A | 3/1987 | Harm et al. |
| 4,674,320 A | 6/1987 | Hirschfeld |
| 4,777,599 A | 10/1988 | Dorogi et al. |
| 4,837,035 A | 6/1989 | Baker |
| 4,874,928 A | 10/1989 | Kasai |
| 4,914,277 A | 4/1990 | Guerin et al. |
| D308,527 S | 6/1990 | Dallman |
| 5,034,242 A | 7/1991 | Lasdon et al. |
| 5,062,066 A | 10/1991 | Scher et al. |
| D333,782 S | 3/1993 | van Berlo |
| 5,250,789 A | 10/1993 | Johnsen |
| 5,361,681 A | 11/1994 | Hedström |
| 5,412,560 A | 5/1995 | Dennision |
| 5,442,669 A | 8/1995 | Medin |
| 5,478,900 A | 12/1995 | Amano et al. |
| 5,478,989 A | 12/1995 | Shepley |
| 5,478,990 A | 12/1995 | Montanari et al. |
| 5,483,799 A | 1/1996 | Dalto |
| 5,496,576 A | 5/1996 | Jeong |
| 5,558,797 A | 9/1996 | Takagi |
| 5,638,285 A | 6/1997 | Newton |
| 5,673,691 A | 10/1997 | Abrams et al. |
| 5,697,177 A | 12/1997 | Ludlow et al. |
| 5,804,803 A | 9/1998 | Cragun et al. |
| 5,853,790 A | 12/1998 | Glancy |
| 5,872,721 A | 2/1999 | Huston et al. |
| 5,877,477 A | 3/1999 | Petty et al. |
| 5,954,640 A | 9/1999 | Szabo |
| 6,012,415 A | 1/2000 | Linseth |
| 6,080,972 A | 6/2000 | May |
| 6,119,531 A | 9/2000 | Wendte et al. |
| 6,157,306 A | 12/2000 | Mularoni |
| 6,182,725 B1 | 2/2001 | Sorvik |
| 6,211,789 B1 | 4/2001 | Oldham et al. |
| 6,270,724 B1 | 8/2001 | Woodaman |
| 6,276,264 B1 | 8/2001 | Dumm |
| 6,285,282 B1 | 9/2001 | Dorenbosch et al. |
| 6,299,920 B1 | 10/2001 | Saskena |
| 6,299,921 B1 | 10/2001 | Loffler et al. |
| 6,310,964 B1 | 10/2001 | Mohan et al. |
| 6,325,878 B1 | 12/2001 | Borgstrom |
| 6,356,940 B1 | 3/2002 | Short |
| 6,375,077 B1 | 4/2002 | Hankins |
| 6,387,049 B1 | 5/2002 | Moore |
| 6,444,233 B1 | 9/2002 | Arntzen et al. |
| 6,483,434 B1 | 11/2002 | Umiker |
| 6,491,217 B2 | 12/2002 | Catan |
| D468,755 S | 1/2003 | Muniz-Rivera et al. |
| 6,502,411 B2 | 1/2003 | Okamoto |
| 6,512,919 B2 | 1/2003 | Ogasawara |
| 6,513,532 B2 | 2/2003 | Mault et al. |
| 6,538,215 B2 | 3/2003 | Montagnino et al. |
| 6,549,818 B1 | 4/2003 | Ali |
| 6,553,386 B1 | 4/2003 | Alabaster |
| 6,554,182 B1 | 4/2003 | Magnusson et al. |
| 6,556,963 B1 | 4/2003 | Tetzlaff |
| 6,571,603 B1 | 6/2003 | Doleman et al. |
| 6,591,738 B2 * | 7/2003 | Gabriel ............... G01K 3/04 374/E3.004 |
| D478,773 S | 8/2003 | Palen |
| 6,616,047 B2 | 9/2003 | Catan |
| 6,631,333 B1 | 10/2003 | Lewis et al. |
| 6,671,698 B2 | 12/2003 | Pickett et al. |
| 6,676,014 B2 | 1/2004 | Catan |
| 6,689,398 B2 | 2/2004 | Haridas et al. |
| 6,691,135 B2 | 2/2004 | Pickett et al. |
| 6,716,462 B2 | 4/2004 | Prosise et al. |
| 6,759,635 B2 * | 7/2004 | Lile ............ A47J 27/62 219/494 |
| 6,773,926 B1 | 8/2004 | Freund et al. |
| 6,789,021 B2 | 9/2004 | Rendahl et al. |
| 6,809,301 B1 | 10/2004 | McIntyre et al. |
| 6,844,197 B1 | 1/2005 | Doleman et al. |
| 6,850,861 B1 * | 2/2005 | Faiola ............... G01K 1/026 374/E1.005 |
| 6,874,000 B2 | 3/2005 | Sholl et al. |
| 6,888,458 B2 | 5/2005 | Carlson |
| 6,953,342 B2 | 10/2005 | Bisogno |
| 6,953,919 B2 | 10/2005 | Clothier |
| 6,975,910 B1 | 12/2005 | Brown et al. |
| 6,982,640 B2 | 1/2006 | Lindsay et al. |
| 7,024,369 B1 | 4/2006 | Brown et al. |
| 7,076,438 B1 | 7/2006 | Tobelmann et al. |
| 7,080,593 B1 | 7/2006 | Frankel |
| 7,085,777 B2 | 8/2006 | Beck et al. |
| 7,090,638 B2 | 8/2006 | Vidgen |
| 7,103,481 B2 | 9/2006 | Negri |
| 7,151,447 B1 | 12/2006 | Willms et al. |
| 7,152,040 B1 | 12/2006 | Hawthorne et al. |
| D534,758 S | 1/2007 | Lee et al. |
| D539,072 S | 3/2007 | Kawata et al. |
| D539,595 S | 4/2007 | Okuda et al. |
| D540,613 S | 4/2007 | Jeon |
| D540,831 S | 4/2007 | Kim et al. |
| D541,578 S | 5/2007 | Jeon |
| 7,212,955 B2 | 5/2007 | Kirshenbaum et al. |
| 7,213,743 B2 | 5/2007 | Carlson et al. |
| 7,215,420 B2 | 5/2007 | Gellerman et al. |
| 7,237,400 B2 | 7/2007 | Owada |
| 7,256,699 B2 | 8/2007 | Tethrake et al. |
| 7,275,863 B1 | 10/2007 | Akers et al. |
| 7,295,889 B2 | 11/2007 | Lahteenmaki |
| D560,960 S | 2/2008 | Hillmann et al. |
| 7,326,888 B2 | 2/2008 | Chun et al. |
| 7,348,522 B1 * | 3/2008 | Criscuolo ............... F24C 15/16 165/61 |
| 7,349,857 B2 | 3/2008 | Manzo |
| D567,828 S | 4/2008 | Moran |
| 7,357,316 B2 | 4/2008 | Heckel et al. |
| 7,359,802 B1 | 4/2008 | Lewis et al. |
| 7,372,003 B2 | 5/2008 | Kates |
| 7,396,550 B2 | 7/2008 | Angel |
| 7,403,855 B2 | 7/2008 | Fuessley et al. |
| 7,440,901 B1 | 10/2008 | Dlott et al. |
| 7,445,372 B1 | 11/2008 | Engel et al. |
| 7,474,965 B2 | 1/2009 | Johnson et al. |
| 7,509,839 B2 | 3/2009 | Duranton |
| 7,532,106 B2 | 5/2009 | Debord et al. |
| 7,571,676 B2 | 8/2009 | Nelson et al. |
| 7,620,531 B1 | 11/2009 | Johnson |
| D607,264 S | 1/2010 | Lee |
| 7,681,383 B2 | 3/2010 | Argetsinger et al. |
| 7,724,154 B2 * | 5/2010 | Stewart ............... G01K 1/022 340/539.27 |
| D618,488 S | 6/2010 | Knochner |
| 7,743,591 B2 | 6/2010 | Meier et al. |
| 7,797,204 B2 | 9/2010 | Balent |
| 7,809,601 B2 | 10/2010 | Shaya et al. |
| 7,836,876 B2 | 11/2010 | Schellenberg |
| 7,840,359 B2 | 11/2010 | Hsiung et al. |
| 7,854,108 B2 | 12/2010 | Koselka et al. |
| D633,326 S | 3/2011 | Shin et al. |
| 7,933,733 B2 | 4/2011 | Ashrafzadeh et al. |
| 7,942,867 B2 | 5/2011 | Hood et al. |
| 7,951,079 B1 | 5/2011 | Moore |
| 7,957,850 B2 | 6/2011 | Anderson |
| 7,996,134 B2 | 8/2011 | Roberts |
| 8,009,048 B2 | 8/2011 | Hyde et al. |
| 8,033,237 B2 | 10/2011 | Havens et al. |
| 8,082,809 B2 | 12/2011 | Luellen et al. |
| D654,299 S | 2/2012 | Benold |
| 8,112,303 B2 | 2/2012 | Eglen et al. |
| D657,607 S | 4/2012 | Ohmae et al. |
| 8,147,888 B2 | 4/2012 | Kling et al. |
| 8,173,188 B2 | 5/2012 | Suetsugu |
| D662,525 S | 6/2012 | Moseley |
| 8,193,474 B2 | 6/2012 | Harris |
| D665,220 S | 8/2012 | Ohmae et al. |
| 8,265,957 B2 | 9/2012 | Craine |
| 8,285,593 B2 | 10/2012 | Bhatt et al. |
| 8,314,701 B2 | 11/2012 | Grieco et al. |
| D673,001 S | 12/2012 | Becze et al. |

(56) References Cited

U.S. PATENT DOCUMENTS

| | | |
|---|---|---|
| 8,393,137 B1 | 3/2013 | Crosby |
| 8,403,215 B2 | 3/2013 | Aihara et al. |
| 8,490,862 B1 | 7/2013 | Minvielle |
| 8,550,365 B1 | 10/2013 | Minvielle |
| 8,626,796 B2 | 1/2014 | McBride et al. |
| 8,631,050 B1 | 1/2014 | Gayle |
| 8,668,140 B2 | 3/2014 | Minvielle |
| D702,482 S | 4/2014 | Davis et al. |
| 8,733,631 B2 | 5/2014 | Minvielle |
| 8,783,556 B2 | 7/2014 | Minvielle |
| 8,788,341 B1 | 7/2014 | Patel |
| 8,796,510 B2 | 8/2014 | Heard et al. |
| 8,825,516 B2 | 9/2014 | Grant et al. |
| 8,851,365 B2 | 10/2014 | Minvielle |
| 8,864,042 B2 * | 10/2014 | Brock ............... B60H 1/00978 236/94 |
| 8,931,400 B1 * | 1/2015 | Allen ..................... H04Q 9/00 340/870.09 |
| 9,016,193 B2 | 4/2015 | Minvielle |
| 9,080,997 B2 | 7/2015 | Minvielle |
| 9,084,566 B2 | 7/2015 | Zdeblick |
| 9,165,320 B1 | 10/2015 | Belvin |
| 9,241,909 B2 | 1/2016 | Selanikio |
| 9,364,106 B1 | 6/2016 | Ortiz |
| 9,386,738 B2 | 7/2016 | Peterson et al. |
| 2002/0004749 A1 | 1/2002 | Froseth et al. |
| 2002/0005412 A1 | 1/2002 | Laforcade |
| 2002/0011567 A1 | 1/2002 | Ozanich |
| 2002/0040564 A1 | 4/2002 | Killingbeck et al. |
| 2002/0059175 A1 | 5/2002 | Nakano |
| 2002/0072932 A1 | 6/2002 | Swamy |
| 2002/0085164 A1 | 7/2002 | Stanford-Clark |
| 2002/0091593 A1 | 7/2002 | Fowler |
| 2002/0106432 A1 | 8/2002 | Yamagata et al. |
| 2002/0123070 A1 | 9/2002 | Hsieh |
| 2002/0125313 A1 | 9/2002 | Broff |
| 2002/0163436 A1 | 11/2002 | Singh et al. |
| 2002/0168456 A1 | 11/2002 | Robbins |
| 2003/0006281 A1 | 1/2003 | Thomas et al. |
| 2003/0027161 A1 | 2/2003 | Bejanin et al. |
| 2003/0036852 A1 | 2/2003 | Ell et al. |
| 2003/0050730 A1 | 3/2003 | Greeven et al. |
| 2003/0099157 A1 | 5/2003 | Quine |
| 2003/0127451 A1 | 7/2003 | Lile |
| 2003/0136960 A1 | 7/2003 | Goodman et al. |
| 2003/0163354 A1 | 8/2003 | Shamoun |
| 2003/0165602 A1 | 9/2003 | Garwood |
| 2003/0185937 A1 | 10/2003 | Garwood |
| 2003/0185948 A1 | 10/2003 | Garwood |
| 2003/0204359 A1 | 10/2003 | Blakley et al. |
| 2003/0227392 A1 | 12/2003 | Ebert et al. |
| 2004/0016348 A1 | 1/2004 | Sharpe |
| 2004/0031335 A1 | 2/2004 | Fromme et al. |
| 2004/0045202 A1 | 3/2004 | Arrendale, III et al. |
| 2004/0083201 A1 | 4/2004 | Sholl et al. |
| 2004/0088330 A1 | 5/2004 | Pickett et al. |
| 2004/0093274 A1 | 5/2004 | Vanska et al. |
| 2004/0100380 A1 | 5/2004 | Lindsay et al. |
| 2004/0130714 A1 | 7/2004 | Gellerman et al. |
| 2004/0147038 A1 | 7/2004 | Lewis et al. |
| 2004/0148117 A1 | 7/2004 | Kirshenbaum et al. |
| 2004/0152131 A1 | 8/2004 | Hsieh |
| 2004/0158447 A1 | 8/2004 | Leger et al. |
| 2004/0167724 A1 | 8/2004 | Federer et al. |
| 2004/0177011 A1 | 9/2004 | Ramsay et al. |
| 2004/0191382 A1 | 9/2004 | Cooper et al. |
| 2004/0201454 A1 | 10/2004 | Waterhouse et al. |
| 2004/0215402 A1 | 10/2004 | Hsiung et al. |
| 2004/0261280 A1 | 12/2004 | Znaiden et al. |
| 2004/0267098 A1 | 12/2004 | Moore |
| 2005/0001728 A1 | 1/2005 | Appelt et al. |
| 2005/0012627 A1 * | 1/2005 | Lion ..................... G01K 1/024 340/584 |
| 2005/0027726 A1 | 2/2005 | Guivarch et al. |
| 2005/0049920 A1 | 3/2005 | Day et al. |
| 2005/0075900 A1 | 4/2005 | Arguimbau, III |
| 2005/0079491 A1 | 4/2005 | Donne-Gousse et al. |
| 2005/0106103 A1 | 5/2005 | Dussaud et al. |
| 2005/0168325 A1 | 8/2005 | Lievre et al. |
| 2005/0171738 A1 | 8/2005 | Kadaba |
| 2005/0184148 A1 | 8/2005 | Perlman |
| 2005/0223905 A1 | 10/2005 | Ghiraldi |
| 2005/0247213 A1 | 11/2005 | Slilaty |
| 2005/0248455 A1 | 11/2005 | Pope et al. |
| 2005/0251449 A1 | 11/2005 | Pape et al. |
| 2006/0015371 A1 | 1/2006 | Knauf et al. |
| 2006/0048588 A1 * | 3/2006 | Howarth ................ G01N 3/48 73/866.5 |
| 2006/0061454 A1 | 3/2006 | Debord et al. |
| 2006/0062835 A1 | 3/2006 | Weil |
| 2006/0073483 A1 | 4/2006 | White et al. |
| 2006/0078658 A1 | 4/2006 | Owens et al. |
| 2006/0099310 A1 | 5/2006 | Koekkoek |
| 2006/0130498 A1 | 6/2006 | Joshi et al. |
| 2006/0172048 A1 | 8/2006 | Etchells et al. |
| 2006/0178841 A1 | 8/2006 | Fernandez |
| 2006/0200480 A1 | 9/2006 | Harris et al. |
| 2006/0201432 A1 | 9/2006 | Pratt |
| 2006/0218057 A1 | 9/2006 | Fitzpatrick et al. |
| 2006/0228428 A1 | 10/2006 | Kang et al. |
| 2006/0240174 A1 | 10/2006 | Jung et al. |
| 2006/0256132 A1 | 11/2006 | Shin et al. |
| 2006/0277064 A1 | 12/2006 | Cannata |
| 2006/0286211 A1 | 12/2006 | Lang |
| 2007/0016852 A1 | 1/2007 | Kim et al. |
| 2007/0036840 A1 | 2/2007 | Tuduri et al. |
| 2007/0049910 A1 | 3/2007 | Altshuler et al. |
| 2007/0050229 A1 | 3/2007 | Tatro et al. |
| 2007/0055551 A1 | 3/2007 | Szabo |
| 2007/0055573 A1 | 3/2007 | Grell |
| 2007/0059402 A1 | 3/2007 | Barmore |
| 2007/0118394 A1 | 5/2007 | Cahoon |
| 2007/0191689 A1 | 8/2007 | Elitok |
| 2007/0204691 A1 | 9/2007 | Bogner et al. |
| 2007/0207242 A1 | 9/2007 | Carlsen |
| 2007/0209656 A1 | 9/2007 | Lee |
| 2007/0254080 A1 | 11/2007 | Schackmuith et al. |
| 2007/0258048 A1 | 11/2007 | Pitchers |
| 2007/0269557 A1 | 11/2007 | Culver et al. |
| 2007/0294129 A1 | 12/2007 | Froseth et al. |
| 2007/0298147 A1 | 12/2007 | Haus |
| 2008/0058783 A1 | 3/2008 | Altshuler et al. |
| 2008/0059342 A1 | 3/2008 | Culver et al. |
| 2008/0077455 A1 | 3/2008 | Gilboa |
| 2008/0083825 A1 | 4/2008 | Yang et al. |
| 2008/0091705 A1 | 4/2008 | McBride et al. |
| 2008/0102175 A1 | 5/2008 | Jeon et al. |
| 2008/0158543 A1 | 7/2008 | Puskas et al. |
| 2008/0162186 A1 | 7/2008 | Jones |
| 2008/0167833 A1 | 7/2008 | Matsen et al. |
| 2008/0171120 A1 | 7/2008 | Willett |
| 2008/0183588 A1 | 7/2008 | Agrawal et al. |
| 2008/0186175 A1 | 8/2008 | Stern |
| 2008/0193614 A1 | 8/2008 | Greiner et al. |
| 2008/0195456 A1 | 8/2008 | Fitzpatrick et al. |
| 2008/0254449 A1 | 10/2008 | Plante |
| 2008/0275309 A1 | 11/2008 | Stivoric et al. |
| 2008/0280000 A1 | 11/2008 | Breunig et al. |
| 2008/0295702 A1 | 12/2008 | Wiedemann et al. |
| 2009/0029014 A1 | 1/2009 | Walter et al. |
| 2009/0035392 A1 | 2/2009 | Wilkinson |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0114713 A1 | 5/2009 | Spenik et al. |
| 2009/0132132 A1 | 5/2009 | Peterson et al. |
| 2009/0157460 A1 | 6/2009 | Narayanaswamy |
| 2009/0177068 A1 | 7/2009 | Stivoric et al. |
| 2009/0202700 A1 | 8/2009 | Bunke et al. |
| 2009/0208607 A1 | 8/2009 | Bunke et al. |
| 2009/0210102 A1 | 8/2009 | Thybo et al. |
| 2009/0232958 A1 | 9/2009 | Samoto et al. |
| 2009/0271010 A1 | 10/2009 | Hyde et al. |
| 2009/0275002 A1 | 11/2009 | Hoggle |

(56) References Cited

U.S. PATENT DOCUMENTS

| | | |
|---|---|---|
| 2009/0276912 A1 | 11/2009 | Sherman et al. |
| 2009/0278685 A1 | 11/2009 | Potyrailo et al. |
| 2009/0282004 A1 | 11/2009 | Williams |
| 2009/0283517 A1 | 11/2009 | Mackay et al. |
| 2009/0286212 A1 | 11/2009 | Gordon |
| 2009/0288606 A1 | 11/2009 | Zimmerman |
| 2009/0324785 A1* | 12/2009 | Ceravalls Pujol ....... G01K 1/14 426/231 |
| 2010/0015313 A1 | 1/2010 | Harris |
| 2010/0050667 A1 | 3/2010 | Hall, Jr. et al. |
| 2010/0055259 A1 | 3/2010 | Bourg, Jr. |
| 2010/0055653 A1 | 3/2010 | Miller-Kovach et al. |
| 2010/0070072 A1 | 3/2010 | Goldman et al. |
| 2010/0075436 A1 | 3/2010 | Urdea et al. |
| 2010/0076585 A1 | 3/2010 | Mayer et al. |
| 2010/0076942 A1 | 3/2010 | Lee |
| 2010/0086655 A1 | 4/2010 | Singer |
| 2010/0097193 A1 | 4/2010 | Tang |
| 2010/0102959 A1 | 4/2010 | Ashrafzadeh et al. |
| 2010/0106625 A1 | 4/2010 | McCoy |
| 2010/0106626 A1 | 4/2010 | Ashrafzadeh et al. |
| 2010/0117819 A1 | 5/2010 | Murray |
| 2010/0119659 A1 | 5/2010 | Ovadia et al. |
| 2010/0125419 A1 | 5/2010 | Hyde et al. |
| 2010/0135211 A1 | 6/2010 | Park et al. |
| 2010/0152687 A1 | 6/2010 | Carlozzi |
| 2010/0175886 A1 | 7/2010 | Bohacs et al. |
| 2010/0185064 A1 | 7/2010 | Bandic et al. |
| 2010/0198605 A1 | 8/2010 | Saulet |
| 2010/0213187 A1 | 8/2010 | Bandholz et al. |
| 2010/0216098 A1 | 8/2010 | Montgomery |
| 2010/0216136 A1 | 8/2010 | B.Che Man et al. |
| 2010/0218044 A1 | 8/2010 | Roblett et al. |
| 2010/0222938 A1 | 9/2010 | Weng |
| 2010/0228160 A1 | 9/2010 | Schweizer |
| 2010/0250271 A1 | 9/2010 | Pearce et al. |
| 2010/0253519 A1 | 10/2010 | Brackmann et al. |
| 2010/0264205 A1 | 10/2010 | Iida |
| 2010/0268658 A1 | 10/2010 | Medo et al. |
| 2010/0280895 A1 | 11/2010 | Mottola |
| 2010/0281636 A1 | 11/2010 | Ortins et al. |
| 2010/0287057 A1 | 11/2010 | Aihara et al. |
| 2010/0287101 A1 | 11/2010 | Ishikawa et al. |
| 2011/0020785 A1 | 1/2011 | Lowery, Jr. et al. |
| 2011/0029364 A1 | 2/2011 | Roeding et al. |
| 2011/0082711 A1 | 4/2011 | Poeze et al. |
| 2011/0114624 A1 | 5/2011 | Chung et al. |
| 2011/0123689 A1 | 5/2011 | Luckhart et al. |
| 2011/0124096 A1 | 5/2011 | Philipak et al. |
| 2011/0153364 A1 | 6/2011 | Kerr et al. |
| 2011/0197827 A1 | 8/2011 | Chang |
| 2011/0204137 A1 | 8/2011 | Scharfenort et al. |
| 2011/0217205 A1 | 9/2011 | Peeters |
| 2011/0236862 A1 | 9/2011 | Culver et al. |
| 2011/0240730 A1 | 10/2011 | Covely |
| 2011/0257496 A1 | 10/2011 | Terashima et al. |
| 2011/0258130 A1 | 10/2011 | Grabiner et al. |
| 2011/0259953 A1 | 10/2011 | Baarman et al. |
| 2011/0259960 A1 | 10/2011 | Baarman et al. |
| 2011/0301441 A1 | 12/2011 | Bandic et al. |
| 2011/0302050 A1 | 12/2011 | Kildevaeld |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0005222 A1 | 1/2012 | Bhagwan et al. |
| 2012/0009550 A1 | 1/2012 | Gayle |
| 2012/0016517 A1 | 1/2012 | Holland |
| 2012/0016814 A1 | 1/2012 | Evans |
| 2012/0027897 A1 | 2/2012 | Innocenzi |
| 2012/0045540 A1* | 2/2012 | Lee ................ F25D 29/00 426/7 |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0097050 A1* | 4/2012 | Schaefer et al. ............. 99/468 |
| 2012/0105424 A1 | 5/2012 | Lee et al. |
| 2012/0135455 A1 | 5/2012 | Nerin De La Puerta et al. |
| 2012/0152406 A1 | 6/2012 | Bartholomew et al. |
| 2012/0169469 A1 | 7/2012 | Butler et al. |
| 2012/0173269 A1 | 7/2012 | Omidi |
| 2012/0179665 A1 | 7/2012 | Baarman et al. |
| 2012/0189745 A1* | 7/2012 | DeLong ................ A47J 36/165 426/231 |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1 | 11/2012 | Sandvick |
| 2012/0277180 A1 | 11/2012 | Marini et al. |
| 2012/0290051 A1 | 11/2012 | Boyden et al. |
| 2012/0315609 A1 | 12/2012 | Miller-Kovach et al. |
| 2012/0321759 A1 | 12/2012 | Marinkovich et al. |
| 2013/0030944 A1 | 1/2013 | Nicod et al. |
| 2013/0033031 A1 | 2/2013 | Key |
| 2013/0036001 A1 | 2/2013 | Wegner et al. |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080098 A1 | 3/2013 | Hadad et al. |
| 2013/0080784 A1 | 3/2013 | Oertli |
| 2013/0105565 A1 | 5/2013 | Kamprath |
| 2013/0117310 A1 | 5/2013 | Chai et al. |
| 2013/0209615 A1 | 8/2013 | Lee et al. |
| 2013/0231711 A1 | 9/2013 | Kaib |
| 2013/0255507 A1 | 10/2013 | Meunier et al. |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273222 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0287060 A1 | 10/2013 | Langdoc et al. |
| 2013/0290364 A1 | 10/2013 | Minvielle |
| 2013/0295532 A1 | 11/2013 | Minvielle |
| 2013/0297642 A1 | 11/2013 | Minvielle |
| 2013/0302483 A1 | 11/2013 | Riefenstein |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |
| 2013/0327231 A1 | 12/2013 | Holman et al. |
| 2013/0337516 A1 | 12/2013 | Herrema |
| 2014/0018636 A1 | 1/2014 | Contant et al. |
| 2014/0026762 A1 | 1/2014 | Riefenstein |
| 2014/0037805 A1 | 2/2014 | Minvielle |
| 2014/0038140 A1 | 2/2014 | Minvielle |
| 2014/0041530 A1* | 2/2014 | Luckhardt ................ F24C 7/08 99/333 |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0091136 A1 | 4/2014 | Ybarra, Jr. |
| 2014/0191025 A1 | 7/2014 | Minvielle |
| 2014/0214714 A1 | 7/2014 | Minvielle |
| 2014/0236359 A1 | 8/2014 | Minvielle |
| 2014/0263640 A1 | 9/2014 | Heit et al. |

(56) References Cited

U.S. PATENT DOCUMENTS

| | | |
|---|---|---|
| 2014/0279088 A1 | 9/2014 | Hurst et al. |
| 2014/0290395 A1 | 10/2014 | Minvielle |
| 2014/0290396 A1 | 10/2014 | Minvielle |
| 2014/0339296 A1 | 11/2014 | McAdams et al. |
| 2014/0364971 A1 | 12/2014 | Minvielle |
| 2014/0364972 A1 | 12/2014 | Minvielle |
| 2015/0012122 A1 | 1/2015 | Minvielle |
| 2015/0017252 A1 | 1/2015 | Garland et al. |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100350 A1 | 4/2015 | Minvielle |
| 2015/0100462 A1 | 4/2015 | Minvielle |
| 2015/0149120 A1 | 5/2015 | Burkhardt et al. |
| 2015/0227887 A1 | 8/2015 | Minvielle |
| 2015/0235566 A1 | 8/2015 | Minvielle |
| 2015/0236913 A1 | 8/2015 | Nakano et al. |
| 2015/0320808 A1 | 11/2015 | Burcelin et al. |
| 2016/0171514 A1 | 6/2016 | Frank et al. |
| 2016/0260352 A1 | 9/2016 | Ortiz |
| 2016/0358121 A1 | 12/2016 | Knobel |
| 2018/0232689 A1 | 8/2018 | Minvielle |
| 2018/0284093 A1 | 10/2018 | Minvielle |

FOREIGN PATENT DOCUMENTS

| | | |
|---|---|---|
| DE | 19843016 A1 | 3/2000 |
| DE | 10 2005 040206 A1 | 2/2007 |
| DE | 10 2007 032 303 | 1/2008 |
| EP | 1117055 A2 | 7/2001 |
| EP | 1 253 203 A1 | 10/2002 |
| FR | 2813683 A1 | 3/2002 |
| GB | 2312054 A | 10/1997 |
| WO | WO 91/13304 A1 | 9/1991 |
| WO | WO 02/06984 | 1/2002 |
| WO | 02/37375 A1 | 5/2002 |
| WO | WO 2007/108906 A2 | 9/2007 |
| WO | WO 2008/054231 A1 | 5/2008 |
| WO | 2009/157750 | 12/2009 |
| WO | WO 2013/126579 A1 | 8/2013 |
| WO | 2013/134325 A1 | 9/2013 |
| WO | WO 2013/134544 A1 | 9/2013 |
| WO | WO 2013/142218 A1 | 9/2013 |
| WO | 2013/158571 A2 | 10/2013 |
| WO | 2013/158572 A2 | 10/2013 |
| WO | 2013/158576 A1 | 10/2013 |
| WO | 2013/176800 A1 | 11/2013 |
| WO | WO 2013/180925 A2 | 12/2013 |
| WO | 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | 2015/069325 A1 | 5/2015 |
| WO | 2015/069950 A1 | 5/2015 |
| WO | WO 2017/047842 A1 | 3/2017 |

OTHER PUBLICATIONS

Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf ).
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Office Action in U.S. Appl. No. 13/485,863, dated Feb. 9, 2015.
Office Action in U.S. Appl. No. 13/485,883, dated Feb. 3, 2015.
Office Action in U.S. Appl. No. 13/485,900, dated Feb. 3, 2015.
Office Action in U.S. Appl. No. 13/684,113, dated Dec. 15, 2014.
Office Action in U.S. Appl. No. 13/771,004, dated Mar. 10, 2015.
Office Action in U.S. Appl. No. 13/861,300 dated Feb. 24, 2015.
Office Action in U.S. Appl. No. 13/931,733, dated Mar. 10, 2015.
Office Action in U.S. Appl. No. 14/044,851, dated Jan. 5, 2015.
Notice of Allowance in U.S. Appl. No. 14/059,441, dated Jan. 5, 2015.
Notice of Allowance in U.S. Appl. No. 14/137,963, dated Jan. 28, 2015.
Office Action in U.S. Appl. No. 14/304,671, dated Feb. 4, 2015.
PCT International Search Report and Written Opinion in International Application No. PCT/US2014/033084, dated Mar. 6, 2015.
PCT International Search Report and Written Opinion in International Application No. PCT/US2014/045807, dated Jan. 22, 2015.
PCT International Search Report and Written Opinion in International Application No. PCT/US14/59186, dated Dec. 22, 2014.
PCT International Search Report and Written Opinion in International Application No. PCT/US2014/064434, dated Feb. 20, 2015.
Communication Pursuant to Article 94(3) in European Application No. 13731655.0, dated Jan. 22, 2015.
Extended European Search Report in European Application No. 13751912.0, dated Feb. 25, 2015.
Office Action in U.S. Appl. No. 13/485,850, dated Mar. 19, 2015.
Office Action in U.S. Appl. No. 13/485,866, dated May 7, 2015.
Office Action in U.S. Appl. No. 13/485,883, dated May 20, 2015.
Office Action in U.S. Appl. No. 13/485,916, dated Mar. 27, 2015.
Office Action in U.S. Appl. No. 13/646,632, dated Mar. 26, 2015.
Office Action in U.S. Appl. No. 13/685,575, dated May 5, 2015.
Office Action in U.S. Appl. No. 13/888,353, dated Mar. 26, 2015.
Notice of Allowance in U.S. Appl. No. 13/921,078, dated Apr. 1, 2015.
Notice of Allowance in U.S. Appl. No. 14/044,851, dated Mar. 31, 2015.
Office Action in U.S. Appl. No. 14/203,353, dated Mar. 31, 2015.
Office Action in U.S. Appl. No. 14/260,115, dated Apr. 16, 2015.
Office Action in U.S. Appl. No. 14/466,805, dated Apr. 13, 2015.
Office Action in U.S. Appl. No. 14/286,627, dated Apr. 24, 2015.
Office Action in U.S. Appl. No. 14/466,824, dated May 7, 2015.
Office Action in U.S. Appl. No. 14/467,433, dated May 8, 2015.
Notice of Allowance in U.S. Appl. No. 14/306,111, dated Mar. 17, 2015.
PCT International Search Report and Written Opinion in International Application No. PCT/US2014/044700, dated May 18, 2015.
PCT International Search Report and Written Opinion in International Application No. PCT/US2014/065281, dated Mar. 13, 2015.
Office Action in U.S. Appl. No. 14/137,963, dated Aug. 5, 2014.
Restriction Requirement in U.S. Appl. No. 13/684,113, dated Sep. 5, 2014.
Thakur, M. et al., "Food Traceability, R&D Norway" Food Technology, Apr. 2012, p. 42-46.
Hoffman, B., "IBM Announces Food Traceability Technology," Food+Tech Connect, Oct. 19, 2011, 2 pages.
"SIRA Technologies Food Sentinel System Thermal Barcode for Packaging," Sustainable is Good: Lifestyle and Design blog, Mar. 4, 2009, 2 pages.
Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Chaudhry, Q. et al., "Applications and Implications of Nanotechnologies for the Food Sector", Food Additives and Contaminants. Part A, Mar. 2008, vol. 25, Issue 3, pp. 241-258.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
Diller, K.R., "Stress Protein Expression Kinetics", Annual Review of Biomedical Engineering, 2006, vol. 8, pp. 403-424.

(56) References Cited

OTHER PUBLICATIONS

Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Extended European Search Report in European Application No. 13731655.0, dated Feb. 24, 2014.
Extended European Search Report in European Application No. 13757669.0, dated Jan. 31, 2014.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Garcia-Gonzalez, D.L. et al., "Research in Olive Oil: Challenges for the Near Future", Journal of Agricultural and Food Chemistry, 2010, vol. 58 (24), pp. 12569-12577.
Ghasemi-Varnamkhasti, M. et al., "Biomimetic-based odor and taste sensing systems to food quality and safety characterization: An overview on basic principles and recent achievements", Journal of Food Engineering, vol. 100, pp. 377-387, May 2010.
Grate, J.W., "Acoustic Wave Microsensor Arrays for Vapor Sensing", Chemical Reviews, 2000, vol. 100, No. 7, pp. 2627-2647.
Greenfield, H. et al., "Food composition data," FAO, 2003 ("FAO").
Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Hierlemann, A. et al., "Higher-Order Chemical Sensing", Chemical Reviews, 2008, vol. 108, No. 2, pp. 563-613.
Hsieh, Meng-Da et al., "Limits of Recognition for Simple Vapor Mixtures Determined with a Microsensor Array", Analytical Chemistry, Apr. 1, 2004, vol. 76, No. 7, pp. 1885-1895.
James, D. et al., "Chemical Sensors for Electronic Nose Systems", Microchimica Acta, Feb. 2005, vol. 149, pp. 1-17.
Janata, J. et al., "Conducting Polymers in Electronic Chemical Sensors", Nature Materials, Jan. 2003, vol. 2, pp. 19-24.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Kingsmore, S.F., "Multiplexed Protein Measurement: Technologies and Applications of Protein and Antibody Arrays", Nature Reviews Drug Discovery, Apr. 2006, vol. 5, pp. 310-321.
Lago, Fatima C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, Fatima C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Martins-Lopes, P. et al., "DNA Markers for Portuguese Olive Oil Fingerprinting", Journal of Agricultural and Food Chemistry, 2008, vol. 56 (24), pp. 11786-11791.
Montealegre, C. et al., "Traceability Markers to the Botanical Origin in Olive Oils", Journal of Agricultural and Food Chemistry, 2010, vol. 58 (1), pp. 28-38.
Montesinos, E., "Plant-associated Microorganisms: a View from the Scope of Microbiology", International Microbiology, (2003), vol. 6, Issue 4, pp. 221-223.
Ni, Fu-Tai et al., "Gene Expression and Regulation of Higher Plants Under Soil Water Stress", Current Genomics, Jun. 2009, vol. 10, pp. 269-280.

Notice from the European Patent Office, dated Oct. 1, 2007, concerning business methods, Official Journal EPO, pp. 592-593.
Notice of Allowance in U.S. Appl. No. 13/560,965, dated Mar. 22, 2013.
Notice of Allowance in U.S. Appl. No. 13/750,804, dated May 31, 2013.
Notice of Allowance in U.S. Appl. No. 13/900,426, dated Dec. 16, 2013.
Notice of Allowance in U.S. Appl. No. 13/931,744, dated Feb. 28, 2014.
Notice of Allowance in U.S. Appl. No. 14/047,817, dated Apr. 14, 2014.
Notice of Allowance in U.S. Appl. No. 14/074,664, dated Jun. 2, 2014.
Office Action in U.S. Appl. No. 13/485,850, dated Mar. 20, 2014.
Office Action in U.S. Appl. No. 13/485,850, dated May 9, 2013.
Office Action in U.S. Appl. No. 13/485,850, dated Sep. 30, 2013.
Office Action in U.S. Appl. No. 13/485,878, dated Jun. 5, 2014.
Office Action in U.S. Appl. No. 13/485,878, dated Oct. 24, 2013.
Office Action in U.S. Appl. No. 13/560,965, dated Feb. 1, 2013.
Office Action in U.S. Appl. No. 13/602,040, dated Jan. 11, 2013 (restriction).
Office Action in U.S. Appl. No. 13/602,040, dated Jul. 17, 2014.
Office Action in U.S. Appl. No. 13/602,040, dated Oct. 23, 2013.
Office Action in U.S. Appl. No. 13/685,575, dated May 6, 2013.
Office Action in U.S. Appl. No. 13/685,575, dated Oct. 24, 2013.
Office Action in U.S. Appl. No. 13/732,050, dated Apr. 10, 2014.
Office Action in U.S. Appl. No. 13/732,050, dated Oct. 24, 2013.
Office Action in U.S. Appl. No. 13/750,804, dated Mar. 12, 2013.
Office Action in U.S. Appl. No. 13/771,004, dated Apr. 4, 2014.
Office Action in U.S. Appl. No. 13/771,004, dated Jul. 8, 2013.
Office Action in U.S. Appl. No. 13/771,004, dated May 15, 2013.
Office Action in U.S. Appl. No. 13/888,353, dated Dec. 4, 2013 (restriction).
Office Action in U.S. Appl. No. 13/888,353, dated Jul. 25, 2013 (restriction).
Office Action in U.S. Appl. No. 13/888,353, dated May 1, 2014.
Office Action in U.S. Appl. No. 13/900,426, dated Aug. 8, 2013.
Office Action in U.S. Appl. No. 13/931,744, dated Aug. 20, 2013.
Office Action in U.S. Appl. No. 13/937,167, dated Apr. 14, 2014.
Office Action in U.S. Appl. No. 13/937,167, dated Oct. 28, 2013.
Office Action in U.S. Appl. No. 13/948,004, dated Jun. 11, 2014.
Office Action in U.S. Appl. No. 13/948,004, dated Oct. 24, 2013.
Office Action in U.S. Appl. No. 14/047,817, dated Nov. 29, 2013.
Office Action in U.S. Appl. No. 14/059,441 dated Jul. 10, 2014.
Office Action in U.S. Appl. No. 14/059,441, dated Dec. 20, 2013.
Office Action in U.S. Appl. No. 14/059,441, dated Feb. 11, 2014.
Office Action in U.S. Appl. No. 14/074,664, dated Jan. 8, 2014.
PCT International Search Report and Written Opinion in International Application No. PCT/US2013/029686, dated May 13, 2013.
PCT International Search Report and Written Opinion in International Application No. PCT/US2013/031106, dated May 31, 2013.
PCT International Search Report and Written Opinion in International Application No. PCT/US2013/27148, dated Jun. 18, 2013.
PCT International Search Report and Written Opinion in International Application No. PCT/US2013/29219, dated Jun. 20, 2013.
PCT International Search Report and Written Opinion in International Application No. PCT/US2013/36666, dated Oct. 4, 2013.
PCT International Search Report and Written Opinion in International Application No. PCT/US2013/036668, dated Dec. 6, 2013.
PCT International Search Report and Written Opinion in International Application No. PCT/US2013/036670, dated Aug. 19, 2013.
PCT International Search Report and Written Opinion in International Application No. PCT/US2013/036673, dated Aug. 20, 2013.
PCT International Search Report and Written Opinion in International Application No. PCT/US2013/040445, dated Oct. 25, 2013.
Perks, B., "Fighting Food Fraud with Science", Text Reproduced from Chemistry World, 2007, vol. 4 (9), pp. 48-52.
Preechaburana, P. et al., "Surface plasmon resonance chemical sensing on cell phones", Angew. Chem Int. Ed. 2012, 51, pp. 11585-11588.

(56) References Cited

OTHER PUBLICATIONS

Primrose, S. et al., "Food Forensics: Methods for Determining the Authenticity of Foodstuffs", Trends in Food Science & Technology, Dec. 2010, vol. 21 (12), pp. 582-590.
Rashidi, L. et al., "The Applications of Nanotechnology in Food Industry", Critical Reviews in Food Science and Nutrition, 2011, vol. 51, Issue 8, pp. 723-730.
Restriction Requirement in U.S. Appl. No. 14/137,963, dated May 7, 2014.
Röck, F. et al., "Electronic Nose: Current Status and Future Trends", Chemical Reviews, 2008, vol. 108, No. 2, pp. 705-725.
Sinclair, D.A. et al., "Unlocking the Secrets of Longevity Genes", Scientific American, Mar. 2006, vol. 294, Issue 3, pp. 48-57.
Srinivas, P.R. et al., "Nanotechnology Research: Applications in Nutritional Sciences", The Journal of Nutrition, Symposium—Nanotechnology Research: Applications in Nutritional Sciences, Jan. 2010, vol. 140, No. 1, pp. 119-124.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Statement in accordance with the Notice from the European Patent Office, dated Oct. 1, 2007, concerning business methods.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
U.S. Appl. No. 14/260,115, filed Apr. 23, 2014. (Matter 136).
U.S. Appl. No. 14/286,627, filed May 23, 2014. (Matter 146).
U.S. Appl. No. 14/306,111, filed Jun. 16, 2014. (Matter 151).
U.S. Appl. No. 14/307,365, filed Jun. 17, 2014. (Matter 152).
Walt, D.R., "Electronic Noses: Wake Up and Smell the Coffee", Analytical Chemistry, Feb. 1, 2005, vol. 77 (3), p. A-45.
Wolfbeis, O.S., "Materials for Fluorescence-based Optical Chemical Sensors", Journal of Materials Chemistry, 2005, vol. 15, pp. 2657-2669.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Zou, Ming-Qiang et al., "Rapid Authentication of Olive Oil Adulteration by Raman Spectrometry", Journal of Agricultural and Food Chemistry, 2009, vol. 57 (14), pp. 6001-6006.
Office Action in U.S. Appl. No. 13/485,850, dated Sep. 29, 2014.
Advisory Action in U.S. Appl. No. 13/485,878, dated Sep. 16, 2014.
Office Action in U.S. Appl. No. 13/888,353, dated Oct. 1, 2014.
PCT International Search Report and Written Opinion in International Application No. PCT/US2014/044696, dated Oct. 10, 2014.
PCT International Search Report and Written Opinion in International Application No. PCT/US2014/045796, dated Oct. 15, 2014.
PCT International Search Report and Written Opinion in International Application No. PCT/US2014/045798, dated Oct. 15, 2014.
"Automated Fruit Recognition" Fraunhofer, accessed online Nov. 13, 2014 and, available at http://www.iosb.fraunhofer.de/servlet/is/33328/.
Chung, I-C. et al., "A Portable Electrochemical Sensor for Caffeine and (−)Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2018, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.
De Vos, K. et al., "Multiplexed antibody detection with an array of silicon-on-insulator microring resonators", IEEE, Photonics Journal, vol. 1, Issue 4, Oct. 2009, pp. 225-235.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al, "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Focke, M. et al., "Lab-on-a-Foil: microfluidics on thin and flexible films", Lab on a Chip, vol. 10, Issue 11, published online Mar. 19, 2010, pp. 1365-1386.
Gartia, M. et al., "Colorimetric plasmon resonance imaging using nano lycurgus cup arrays", Advanced Optical Materials, vol. 1, Issue 1, Jan. 2013, pp. 68-76.
Huang, et al., "A passive radio•frequency pH sensing tag for wireless food quality monitoring", IEEE Sensors Journal, vol. 12, Issue 3, Mar. 2012, pp. 487-495.
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Scampicchio, M. et al., "Optical nanoprobes based on gold nanoparticles for sugar sensing", Nanotechnology, vol. 20, Issue 13, Apr. 1, 2009, 5 pages.
Zhu, H. et al., "Quantum dot enabled detection of *Escherichia coli* using a cell-phone", Analyst, vol. 137, Issue 11, Jun. 7, 2012, pp. 2541-2544.
Office Action in U.S. Appl. No. 13/685,575, dated Oct. 27, 2014.
Office Action in U.S. Appl. No. 13/729,548, dated Dec. 2, 2014.
Office Action in U.S. Appl. No. 13/921,078, dated Nov. 4, 2014.
Office Action in U.S. Appl. No. 13/931,733, dated Nov. 6, 2014.
Office Action in U.S. Appl. No. 14/306,111, dated Nov. 13, 2014.
Office Action in U.S. Appl. No. 29/497,888, dated Nov. 19, 2014.
European Examination Report in European Application No. 13757669.0, dated Oct. 13, 2014.
PCT International Search Report and Written Opinion in International Application No. PCT/US2014/036570, dated Mar. 10, 2015.
AlKanhal et al., "Changes in protein nutritional quality in fresh and recombined ultra high temperature treated milk during storage.", Int. J. Food Sci. Nutr., Nov. 2001; 52(6): 509-14, 2 pgs.
Office Action in U.S. Appl. No. 13/485,850 dated Sep. 24, 2015.
Office Action in U.S. Appl. No. 13/485,883, dated Oct. 28, 2015.
Office Action in U.S. Appl. No. 13/485,916, dated Sep. 18, 2015.
Office Action in U.S. Appl. No. 13/646,632, dated Oct. 20, 2015.
Office Action in U.S. Appl. No. 13/771,004, dated Oct. 22, 2015.
Office Action in U.S. Appl. No. 13/861,300 dated Sep. 29, 2015.
Office Action in U.S. Appl. No. 13/887,150 dated Nov. 20, 2015.
Office Action in U.S. Appl. No. 14/260,115, dated Dec. 4, 2015.
Office Action in U.S. Appl. No. 14/466,805, dated Nov. 20, 2015.
Office Action in U.S. Appl. No. 14/286,627, dated Oct. 9, 2015.
Office Action in U.S. Appl. No. 14/667,608 dated Nov. 2, 2015.
Office Action in U.S. Appl. No. 14/725,114 dated Oct. 22, 2015.
Further Exam Report in European Application No. 13731655.0, dated Aug. 13, 2015.
Extended European Search Report in European Application No. 13778362.7, dated Nov. 27, 2015.
Extended European Search Report in European Application No. 13777608.4, dated Nov. 19, 2015.
Extended European Search Report in European Application No. 13778042.5, dated Nov. 20, 2015.
PCT International Search Report and Written Opinion in International Application No. PCT/US2015/035875, dated Sep. 4, 2015.

(56) References Cited

OTHER PUBLICATIONS

PCT International Search Report and Written Opinion in International Application No. PCT/US2015/045562, dated Nov. 23, 2015.
Notice of Allowance in U.S. Appl. No. 13/931,733, dated Jun. 11, 2015.
Office Action in U.S. Appl. No. 13/485,863, dated Sep. 2, 2015.
Office Action in U.S. Appl. No. 13/485,878, dated Jul. 8, 2015.
Office Action in U.S. Appl. No. 13/602,040, dated Jul. 6, 2015.
Final Office Action in U.S. Appl. No. 13/684,113, dated Jul. 1, 2015.
Final Office Action in U.S. Appl. No. 13/729,548, dated Jul. 14, 2015.
Office Action in U.S. Appl. No. 13/732,050, dated Jun. 23, 2015.
Office Action in U.S. Appl. No. 13/888,353, dated Sep. 9, 2015.
Office Action in U.S. Appl. No. 13/937,167 dated Aug. 17, 2015.
Office Action in U.S. Appl. No. 13/948,004, dated Jul. 31, 2015.
Office Action in U.S. Appl. No. 13/948,071, dated Jul. 20, 2015.
Office Action in U.S. Appl. No. 13/948,078, dated Aug. 5, 2015.
Office Action in U.S. Appl. No. 14/080,768, dated Jun. 17, 2015.
Office Action in U.S. Appl. No. 14/203,353, dated Aug. 20, 2015.
Office Action in U.S. Appl. No. 14/304,671, dated Sep. 3, 2015.
Office Action in U.S. Appl. No. 29/497,888, dated Jul. 1, 2015.
Search Report and Written Opinion in Singapore application 2013045448 dated Jun. 24, 2015.
Extended European Search Report in European Application No. 13763782.3, dated Jun. 11, 2015.
PCT International Search Report and Written Opinion in International Application No. PCT/US2015/035872, dated Sep. 3, 2015.
Wijtzes, T., et al., "A decision support system for the prediction of microbial food safety and food quality", International Journal of Food Microbiology 42 (1997) 79-90.
Extended European Search Report in European Application No. 13757527.0, dated Mar. 24, 2016.
Qiao, Y, "Routine Techniques for Monitoring the Value of Animal Meals", Unknown, 2001, 224 pgs. https://books.google.com/books/about/Routine_Techniques_for_Monitoring_the_Nu.html?id=LhsktkRPZ7EC (No Copies Available Online Copyright Restricted).
Office Action in U.S. Appl. No. 13/485,863, dated Dec. 30, 2015.
Office Action in U.S. Appl. No. 13/485,866, dated Dec. 24, 2015.
Office Action in U.S. Appl. No. 13/485,878, dated Feb. 1, 2016.
Office Action in U.S. Appl. No. 13/485,916, dated Feb. 18, 2016.
Office Action in U.S. Appl. No. 13/646,632, dated Dec. 31, 2015.
Office Action in U.S. Appl. No. 13/729,548, dated Feb. 5, 2016.
Office Action in U.S. Appl. No. 13/732,050, dated Jan. 15, 2016.
Office Action in U.S. Appl. No. 13/937,167 dated Mar. 2, 2016.
Office Action in U.S. Appl. No. 13/948,004, dated Dec. 17, 2015.
Office Action in U.S. Appl. No. 14/080,768, dated Jan. 25, 2016.
Office Action in U.S. Appl. No. 14/203,353, dated Mar. 7, 2016.
Office Action in U.S. Appl. No. 14/466,805, dated Mar. 8, 2016.
Office Action in U.S. Appl. No. 14/286,627, dated Mar. 3, 2016.
Office Action in U.S. Appl. No. 14/466,824, dated Jan. 13, 2016.
Office Action in U.S. Appl. No. 14/467,433, dated Dec. 24, 2015.
Search Report and Written Opinion in Singapore application 10201406107X dated Feb. 11, 2016.
Extended European Search Report in European Application No. 13793073.1 dated Jan. 14, 2016.
Office Action in U.S. Appl. No. 13/485,883, dated Apr. 19, 2016.
Office Action in U.S. Appl. No. 13/602,040, dated May 6, 2016.
Office Action in U.S. Appl. No. 13/646,632, dated Apr. 21, 2016.
Office Action in U.S. Appl. No. 13/685,575, dated May 11, 2016.
Office Action in U.S. Appl. No. 13/684,113, dated Jun. 8, 2016.
Office Action in U.S. Appl. No. 13/771,004, dated May 31, 2016.
Notice of Allowance in U.S. Appl. No. 13/861,300, dated Apr. 15, 2016.
Office Action in U.S. Appl. No. 13/888,353, dated Apr. 21, 2016.
Office Action in U.S. Appl. No. 14/304,671, dated Apr. 8, 2016.
Office Action in U.S. Appl. No. 14/307,365, dated May 3, 2016.
Office Action in U.S. Appl. No. 14/643,995 dated Jun. 14, 2016.
Office Action in U.S. Appl. No. 14/667,608 dated Mar. 16, 2016.
Office Action in U.S. Appl. No. 14/860,340 dated Apr. 20, 2016.
Office Action in U.S. Appl. No. 14/304,671, dated Mar. 23, 2017.
Office Action in U.S. Appl. No. 14/307,365, dated Dec. 2, 2016.
Office Action in U.S. Appl. No. 14/693,799 dated Mar. 2, 2017.
Abad, E., et al., RFID smart tag for traceability and cold chain monitoring of foods: Demonstration in an intercontinental fresh fish logistic chain; Journal of Food Engineering, Barking, Essex, GB, vol. 93, No. 4; Aug. 1, 2009; pp. 394-399.
Amador, Cecelia, et al., Application of RFID technologies in the temperature mapping of the pineapple supply chain; Sensing and Instrumentation for Food Quality and Safety, vol. 3, No. 1; Mar. 1, 2009; pp. 26-33.
Lang, Walter, et al., The "Intelligent Container"—A Cognitive Sensor Network of Transport Management, IEEE Sensors Journal; IEEE Service Center, New York, NY, US, vol. 11, No. 3; Mar. 1, 2011; pp. 688-698.
Extended European Search Report and Search Opinion in European Patent Application No. 14852115.6 dated Apr. 18, 2017.
Office Action in U.S. Appl. No. 14/304,671, dated Aug. 9, 2017.
Office Action in U.S. Appl. No. 14/307,365, dated Aug. 2, 2017.
Office Action in U.S. Appl. No. 14/385,918, dated Nov. 16, 2017.
Office Action in U.S. Appl. No. 14/693,799 dated Jul. 28, 2017.
Office Action in U.S. Appl. No. 14/693,799 dated Feb. 23, 2018.
Office Action in U.S. Appl. No. 14/304,671, dated Jun. 1, 2018.
Office Action in U.S. Appl. No. 14/385,918, dated Jul. 19, 2018.
PCT International Search Report and Written Opinion in International Application No. PCT/US2018/025284, dated Jun. 11, 2018.
PCT International Search Report and Written Opinion in International Application No. PCT/US2018/018029, dated Jun. 15, 2018.
Office Action in U.S. Appl. No. 13/485,866, dated Jul. 26, 2016.
Office Action in U.S. Appl. No. 13/485,878, dated Aug. 12, 2016.
Office Action in U.S. Appl. No. 13/485,883, dated Sep. 15, 2016.
Notice of Allowance in U.S. Appl. No. 13/729,548, dated Aug. 19, 2016.
Office Action in U.S. Appl. No. 13/887,150 dated Jun. 17, 2016.
Office Action in U.S. Appl. No. 13/948,004, dated Aug. 15, 2016.
Office Action in U.S. Appl. No. 13/948,083, dated Jul. 14, 2016.
Office Action in U.S. Appl. No. 14/080,768, dated Sep. 8, 2016.
Office Action in U.S. Appl. No. 14/304,671, dated Oct. 20, 2016.
Office Action in U.S. Appl. No. 14/203,353, dated Jul. 29, 2016.
Notice of Allowance in U.S. Appl. No. 14/260,115, dated Jun. 21, 2016.
Notice of Allowance in U.S. Appl. No. 14/466,805, dated Aug. 30, 2016.
Notice of Allowance in U.S. Appl. No. 14/286,627, dated Jun. 22, 2016.
Notice of Allowance in U.S. Appl. No. 14/466,824, dated Aug. 12, 2016.
Notice of Allowance in U.S. Appl. No. 14/467,433, dated Jul. 5, 2016.
Office Action in U.S. Appl. No. 15/090,404 dated Sep. 16, 2016.
Notice of Allowance in U.S. Appl. No. 14/667,608 dated Oct. 19, 2016.
Office Action in U.S. Appl. No. 14/725,114 dated Jun. 27, 2016.
Office Action in U.S. Appl. No. 15/241,019 dated Oct. 19, 2016.
First Examination Report issued in Mexican Patent Application No. MX/a/2014/004378 dated Jul. 27, 2016.
First Examination Report issued in Mexican Patent Application No. MX/a/2014/008414 dated Jul. 28, 2016.
First Examination Report issued in Mexican Patent Application No. MX/a/2014/010787 dated Aug. 1, 2016.
PCT International Search Report and Written Opinion in International Application No. PCT/US2016/034763, dated Oct. 11, 2016.

* cited by examiner

PRESERVATION SYSTEM FOR NUTRITIONAL SUBSTANCES

CROSS REFERENCE TO RELATED APPLICATIONS OR PRIORITY CLAIM

This application claims benefit under 35 U.S.C. 119(e) of U.S. Provisional Patent Application Ser. No. 61/624,948 filed Apr. 16, 2012; U.S. Provisional Patent Application Ser. No. 61/624,972, filed Apr. 16, 2012; and U.S. Provisional Patent Application, 61/624,985, filed Apr. 16, 2012, the contents of which are incorporated herein by reference in their entirety.

FIELD OF THE INVENTION

The present inventions relate to collection, transmission, creation and use of information regarding the preservation of nutritional substances.

BACKGROUND OF THE INVENTION

Nutritional substances are traditionally grown (plants), raised (animals) or synthesized (synthetic compounds). Additionally, nutritional substances can be found in a wild, non-cultivated form, which can be caught or collected. While the collectors and creators of nutritional substances generally obtain and/or generate information about the source, history, caloric content and/or nutritional content of their products, they generally do not pass such information along to the users of their products. One reason is the nutritional substance industries have tended to act like "silo" industries. Each group in the food and beverage industry: growers, packagers, processors, distributors, retailers, and preparers work separately, and either shares no information, or very little information, between themselves. There is generally no consumer access to, and little traceability of, information regarding the creation and/or origin, preservation, processing, preparation, or consumption of nutritional substances. It would be desirable for such information be available to the consumers of nutritional substances, as well as all participants in the food and beverage industry—the nutritional substance supply system.

While the nutritional substance supply system has endeavored over the last 50 years to increase the caloric content of nutritional substances produced (which has help reduce starvation in developing countries, but has led to obesity problems in developed countries), maintaining, or increasing, the nutritional content of nutritional substances has been a lower priority. Caloric content refers to the energy in nutritional substances, commonly measured in calories. The caloric content could be represented as sugars and/or carbohydrates in the nutritional substances. The nutritional content of foods and beverages, as used herein, refers to the non-caloric content of these nutritional substances which are beneficial to the organisms which consume these nutritional substances. For example, the nutritional content of a nutritional substance could include vitamins, minerals, proteins, and other non-caloric components which are necessary, or at least beneficial, to the organism consuming the nutritional substances.

While there has recently been greater attention by consumer organizations, health organizations and the public to the nutritional content of foods and beverages, the food and beverage industry has been slow in responding to this attention. One reason for this may be that since the food and beverage industry operates as silos of those who create nutritional substances, those who preserve and transport nutritional substances, those who transform nutritional substances, and those who finally prepare the nutritional substances for consumption by the consumer, there has been no coordination of management of nutritional content. While each of these silo industries may be able to maintain or increase the nutritional content of the foods and beverages they handle, each silo industry has only limited information and control of the nutritional substances they receive, and the nutritional substances they pass along.

As consumers better understand their need for nutritional substances with higher nutritional content, they will start demanding that the food and beverage industry offer products which include higher nutritional content, and/or at least information regarding nutritional content of such products. In fact, consumers are already willing to pay higher prices for higher nutritional content. This can be seen at high-end grocery stores which offer organic, minimally processed, fresh, non-adulterated nutritional substances. Further, as societies and governments seek to improve their constituents' health and lower healthcare costs, incentives and/or mandates will be given to the food and beverage industry to track, maintain, and/or increase the nutritional content of nutritional substances they handle. There will be a need, not only within each food and beverage industry silo to maintain or improve the nutritional content of their products, but an industry-wide solution to allow the management of nutritional content across the entire cycle from creation to consumption. In order to manage the nutritional content of nutritional substances across the entire cycle from creation to consumption, the nutritional substance industry will need to identify, track, measure, estimate, preserve, transform, condition, and record nutritional content for nutritional substances. Of particular importance is the measurement, estimation, and tracking of changes to the nutritional content of a nutritional substance from creation to consumption. This information could be used, not only by the consumer in selecting particular nutritional substances to consume, but could be used by the other food and beverage industry silos, including creation, preservation, transformation, and conditioning, to make decisions on how to create, handle and process nutritional substances. Additionally, those who sell nutritional substances to consumers, such as restaurants and grocery stores, could market and price nutritional substances with higher nutritional content, or minimally degraded nutritional content.

For example, the grower of sweet corn generally only provides basic information as the variety and grade of its corn to the packager, who preserves and ships the corn to a producer for use in a ready-to-eat dinner. The packager may only tell the producer that the corn has been frozen as loose kernels of sweet corn. The producer may only provide the consumer with rudimentary instructions how to cook or reheat the ready-to-eat dinner in a microwave oven, toaster oven or conventional oven, and only tell the consumer that the dinner contains whole kernel corn among the various items in the dinner. Finally, the consumer of the dinner will likely keep her opinions on the quality of the dinner to herself, unless it was an especially bad experience, where she might contact the producer's customer support program to complain. Very minimal, or no, information on the nutritional content of the ready-to-eat dinner is passed along to the consumer. The consumer knows essentially nothing about changes (generally degradation) to the nutritional content of the sweet corn from creation, processing, packaging, cooking, preservation, preparation by consumer, and finally consumption by the consumer.

Consumers' needs are changing as consumers are demanding healthier foods, such as "organic foods." Customers are also asking for more information about the nutritional substances they consume, such as specific characteristics' relating not only to nutritional content, but to allergens or digestive intolerances. For example, nutritional substances which contain lactose, gluten, nuts, dyes, etc. need to be avoided by certain consumers. However, the producer of the ready-to-eat dinner, in the prior example, has very little information to share other than possibly the source of the elements of the ready-to-eat dinner and its processing steps in preparing the dinner. Generally, the producer of the ready-to-eat dinner does not know the nutritional content and organoleptic state of the product after it has been reheated or cooked by the consumer. For example, the consumer may want to know what proportion of organoleptic properties and/or nutritional content the corn in the ready-to-eat dinner remain after cooking or reheating, and the change in nutritional content (usually a degradation). There is a need to preserve, measure, estimate, store and/or transmit such nutritional content information throughout the nutritional substance supply system.

The caloric and nutritional content information for a prepared food that is provided to the consumer is often minimal. For example, when sugar is listed in the ingredient list, the consumer generally does receive any information about the source of the sugar, which can come from a variety of plants, such as sugarcane, beets, or corn, which will affect its nutritional content. Conversely, some nutritional information that is provided to consumers is so detailed, the consumer can do little with it. For example, this of ingredients is from a nutritional label on a consumer product: Vitamins—A 355 IU 7%, E 0.8 mg 4%, K 0.5 mcg, 1%, Thiamin 0.6 mg 43%, Riboflavin 0.3 mg 20%, Niacin 6.0 mg 30%, B6 1.0 mg 52%, Foliate 31.5 mcg 8%, Pantothenic 7%; Minerals Calcium 11.6 1%, Iron 4.5 mg 25%, 211 mg 53%, Phosphorus 349 mg 35%, Potassium 476 mg 14%, Sodium 58.1 mg 2%, Zinc 3.7 mg 24%, Copper 0.5 mg 26%, Manganese 0.8 mg 40%, Selenium 25.7 mcg 37%; Carbohydrate 123 g, Dietary fiber 12.1 g, Saturated fat 7.9 g, Monosaturated Fat 2.1 g, Polysaturated Fat 3.6 g, Omega 3 fatty acids 108 g, Omega 6 fatty acids 3481, Ash 2.0 g and Water 17.2 g. (%=Daily Value). There is a need to provide information about nutritional substances in a meaningful manner. Such information needs to be presented in a manner that meets the specific needs of a particular consumer. For example, consumers with a medical condition, such as diabetes, would want to track specific information regarding sugar and nutrients in the foods and beverages they consume.

If fact, each silo in the food and beverage industry already creates and tracks some information, including caloric and nutritional information, about their product internally. For example, the farmer who grew the corn knows the variety of the seed, condition of the soil, the source of the water, the fertilizers and pesticides used, and can measure the caloric and nutritional content at creation. The packager of the corn knows when it was picked, how it was transported to the packaging plant, how the corn was preserved and packaged before being sent to the ready-to-eat dinner producer, when it was delivered to the producer, and what degradation to caloric and nutritional content has occurred. The producer knows the source of each element of the ready-to-eat dinner, how it was processed, including the recipe followed, and how it was preserved and packaged for the consumer. Not only does such a producer know what degradation to caloric and nutritional occurred, the producer can modify its processing and post-processing preservation to minimally affect nutritional content. The preparation of the nutritional substance for consumption can also degrade the nutritional content of nutritional substances. Finally, the consumer knows how she prepared the dinner, what condiments were added, and whether she did or did not enjoy it.

If there was a mechanism to share this information, the quality of the nutritional substances, including caloric and nutritional content, could be preserved and improved. Consumers could be better informed about nutritional substances they select and consume, including the state of the nutritional substance throughout its lifecycle from creation to consumption. The efficiency and cost effectiveness of nutritional substances could also be improved. Feedback within the entire chain from creator to consumer could provide a closed-loop system that could improve quality (taste, appearance, and caloric and nutritional content), efficiency, value and profit. For example, in the milk supply chain, at least 10% of the milk produced is wasted due to safety margins included in product expiration dates. The use of more accurate tracking information, measured quality (including nutritional content) information, and historical environmental information could substantially reduce such waste. Collecting, preserving, measuring and/or tracking information about a nutritional substance in the nutritional substance supply system, would allow needed accountability. There would be nothing to hide.

As consumers are demanding more information about what they consume, they are asking for products that have higher nutritional content and more closely match good nutritional requirements, and would like nutritional products to actually meet their specific nutritional requirements. While grocery stores, restaurants, and all those who process and sell food and beverages may obtain some information from current nutritional substance tracking systems, such as labels, these current systems can provide only limited information.

Current packaging materials for nutritional substances include plastics, paper, cardboard, glass, and synthetic materials. Generally, the packaging material is chosen by the producer to best preserve the quality of the nutritional substance until used by the customer. In some cases, the packaging may include some information regarding type of nutritional substance, identity of the producer, and the country of origin. Such packaging generally does not transmit source information of the nutritional substance, such as creation information, current or historic information as to the external conditions of the packaged nutritional substance, or current or historic information as to the internal conditions of the packaged nutritional substance.

An important issue in the creation, preservation, transformation, conditioning, and consumption of nutritional substances are the changes that occur in nutritional substances due to a variety of internal and external factors. Because nutritional substances are composed of biological, organic, and/or chemical compounds, they are generally subject to degradation. This degradation generally reduces the nutritional, organoleptic, and/or aesthetic values of nutritional substances. While not always true, nutritional substances are best consumed at their point of creation. However, being able to consume nutritional substances at the farm, at the slaughterhouse, at the fishery, or at the food processing plant is at least inconvenient, if not impossible. Currently, the food and beverage industry attempts to minimize the loss of nutritional value (often through the use of additives or preservatives), and/or attempts to hide this loss of nutritional value from consumers.

Overall, the examples herein of some prior or related systems and their associated limitations are intended to be illustrative and not exclusive. Other limitations of existing or prior systems will become apparent to those of skill in the art upon reading the following Detailed Description.

OBJECTS OF THE INVENTION

It is an object of the present invention to preserve the nutritional substance such that its source information and/or historical preservation information, including external influences on the nutritional substance, are available to users and/or consumers of the nutritional substance.

A further object of the present invention is to provide packaging which interacts with the nutritional substance to maintain and/or improve the nutritional substance being preserved.

It is an object of the present invention to preserve the nutritional substance such that its source information and/or historical preservation information, including external influences on the nutritional substance, are available to users and/or consumers of the nutritional substance.

An object of the present invention, the packaging or label of a nutritional substance tracks creation and historical information of nutritional substance as well as current information about the state of the nutritional substance.

A further object of the present invention is to provide packaging which interacts with the nutritional substance to maintain and/or improve the nutritional substance being preserved.

It is an object of the present invention to preserve the nutritional substance such that its source information and/or historical preservation information, including external influences on the nutritional substance, are available to users and/or consumers of the nutritional substance.

An object of the present invention, the packaging of a nutritional substance tracks creation and historical information of nutritional substance as well as current information about the state of the nutritional substance.

A further object of the present invention is to provide packaging which interacts with the nutritional substance to maintain and/or improve the nutritional substance being preserved.

It is an object of the present invention to minimize and/or track degradation of nutritional, organoleptic, and/or aesthetic value of nutritional substances, and/or collect, store, and/or transmit information regarding this degradation.

SUMMARY OF THE INVENTION

In one embodiment of the present invention, the packaging for a nutritional substance allows for the tracking of source information, information as to the history of the nutritional substance from the point it was packaged and/or current information on outside influences on the packaged nutritional substance.

In another embodiment of the present invention the packaging for the nutritional substance can provide information to the consumer as to the current state of the nutritional substance.

In a further embodiment of the present invention, the packaging of the nutritional substance can interact with the nutritional substance to preserve and/or enhance the nutritional substance.

In one embodiment of the present invention, the packaging for a nutritional substance allows for the tracking of source information, information as to the history of the nutritional substance from the point it was packaged and/or current information on outside influences on the packaged nutritional substance.

In another embodiment of the present invention the packaging/label for the nutritional substance can provide information to the consumer as to the current state of the nutritional substance.

In a further embodiment of the present invention, the packaging of the nutritional substance can interact with the nutritional substance to preserve and/or enhance the nutritional substance.

The an embodiment of the present invention provides a system for the creation, collection, storage, transmission, and/or processing of information regarding nutritional substances so as to improve, maintain, or minimize degradation of nutritional, organoleptic, and/or aesthetic value of nutritional substances. Additionally, the present invention provides such information for use by the creators, preservers, transformers, conditioners, and consumers of nutritional substances. The nutritional information creation, preservation, and transmission system of the present invention should allow the nutritional substance supply system to improve its ability to minimize degradation of nutritional, organoleptic and/or aesthetic value of the nutritional substance, and/or inform the consumer about such degradation. While the ultimate goal of the nutritional substance supply system is to minimize degradation of nutritional, organoleptic and/or aesthetic value, an interim goal should be providing consumers with significant information regarding degradation of nutritional substances consumers select and consume. Entities within the nutritional substance supply system who provide such information regarding nutritional substance degradation will be able to differentiate their products from those who obscure and/or hide such information. Additionally, such entities should be able to charge a premium for products which either maintain their nutritional, organoleptic, and/or aesthetic value, or supply more complete information.

Other advantages and features will become apparent from the following description and claims. It should be understood that the description and specific examples are intended for purposes of illustration only and not intended to limit the scope of the present disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
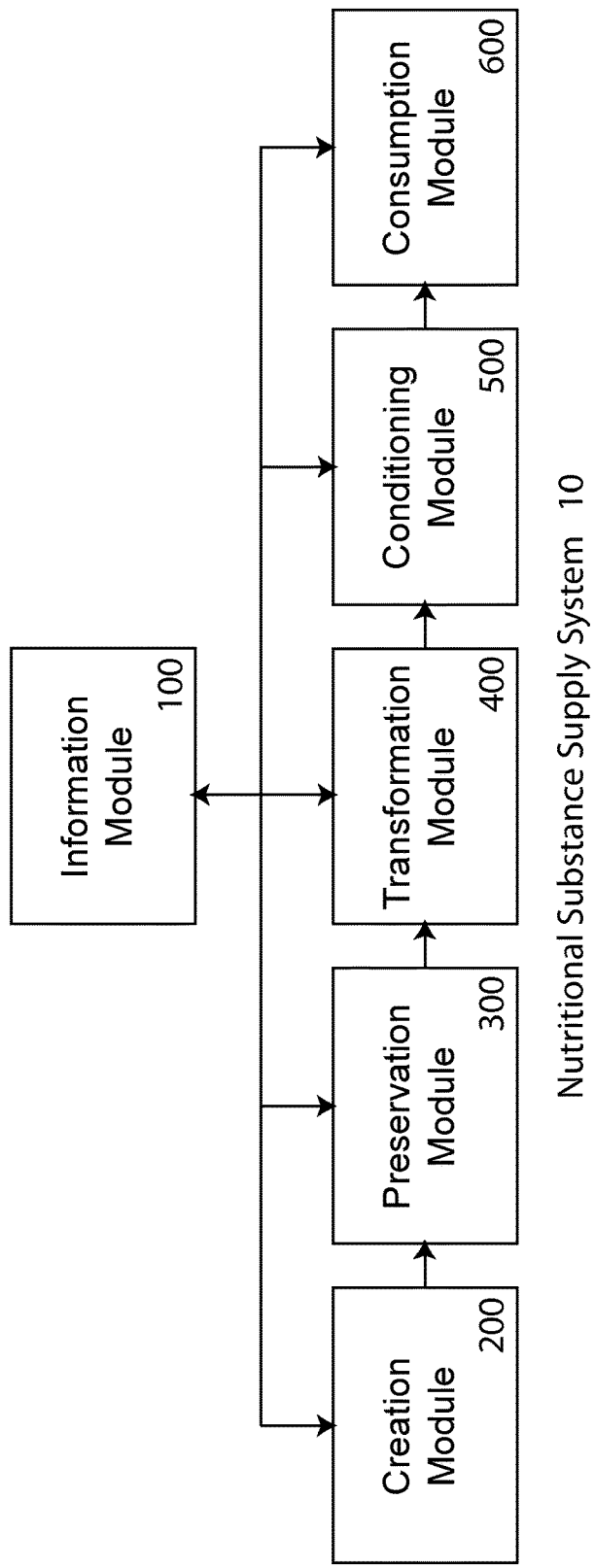
FIG. 1 shows a schematic functional block diagram of a nutritional substance supply relating to the present invention.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION OF THE INVENTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

The following discussion provides a brief, general description of a representative environment in which the invention can be implemented. Although not required, aspects of the invention may be described below in the general context of computer-executable instructions, such as routines executed by a general-purpose data processing device (e.g., a server computer or a personal computer). Those skilled in the relevant art will appreciate that the invention can be practiced with other communications, data processing, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, set-top boxes, network PCs, mini-computers, mainframe computers, and the like. Indeed, the terms "controller," "computer," "server," and the like are used interchangeably herein, and may refer to any of the above devices and systems.

While aspects of the invention, such as certain functions, are described as being performed exclusively on a single device, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analog or digital network (packet switched, circuit switched, or other scheme).

In some instances, the interconnection between modules is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems can be understood to be integrated in some instances and in particular embodiments, only particular modules may be interconnected.

FIG. 1 shows the components of a nutritional substance industry 10. It should be understood that this could be the food and beverage and beverage ecosystem for human consumption, but could also be the feed industry for animal consumption, such as the pet food industry. A goal of the present invention for nutritional substance industry 10 is to create, preserve, transform and trace the qualitative, organoleptic and nutritional properties of nutritional substances through their creation, preservation, transformation, conditioning and consumption. While the nutritional substance industry 10 can be composed of many companies or businesses, it can also be integrated into combinations of business serving many roles, or can be one business or even individual.

Module 200 is the creation module. This can be system, organization, or individual which creates and/or originates nutritional substances. Examples of this module include a farm which grows produce. It can be a ranch which raises beef. It can be an aquaculture far for growing shrimp. It could be a factory with synthesizes nutritional compounds. It could be collector of wild truffles. If could be a deep sea crab trawler.

Preservation module 300 is a preservation system for preserving and protecting the nutritional substances created by creation module 200. Once the nutritional substance has been created, generally, it will need to be packaged in some manner for its transition to other modules in the nutritional substances industry 10. While preservation module 300 is shown in a particular position in the nutritional substance industry 10, following the creation module 200, it should be understood that the preservation module 300 actual can be placed anywhere nutritional substances need to be preserved during their transition from creation to consumption.

Transformation module 400 is a nutritional substance processing system, such as a manufacturer who processes raw materials such as grains into breakfast cereals. Transformation module 400 could also be a ready-to-eat dinner manufacturer who receives the components for a ready-to-eat dinner from preservation module 300 and prepares them into a frozen dinner. While transformation module 400 is depicted as one module, it will be understood that nutritional substances may be transformed by a number of transformation modules 400 on their path to consumption.

Conditioning module 500 is a consumer preparation system for preparing the nutritional substance immediately before consumption by the consumer. Conditioning module 500 can be a microwave oven, a blender, a toaster, a convection oven, a cook, etc. It can also be systems used by commercial establishments to prepare nutritional substance for consumers such as a restaurant, an espresso maker, pizza oven, and other devices located at businesses which provide nutritional substances to consumers. Such nutritional substances could be for consumption at the business or for the consumer to take out from the business. Conditioning module 500 can also be a combination of any of these devices used to prepare nutritional substances for consumption by consumers.

Consumer module 600 collects information from the living entity which consumes the nutritional substance which has passed through the various modules from creation to consumption. The consumer can be a human being, but could also be an animal, such as pets, zoo animals and livestock, which are they themselves nutritional substances for other consumption chains. Consumers could also be plant life which consumes nutritional substances to grow.

Information module 100 receives and transmits information regarding a nutritional substance between each of the modules in the nutritional substance industry 10 including, the creation module 200, the preservation module 300, the transformation module 400, the conditioning module 500, and the consumer module 600. The nutritional substance information module 100 can be an interconnecting information transmission system which allows the transmission of information between various modules. Information module 100 contains a database where the information regarding the nutritional substance resides. Information module 100 can be connected to the other modules by a variety of communication systems, such as paper, computer networks, the internet and telecommunication systems, such as wireless telecommunication systems.

Figure 2:
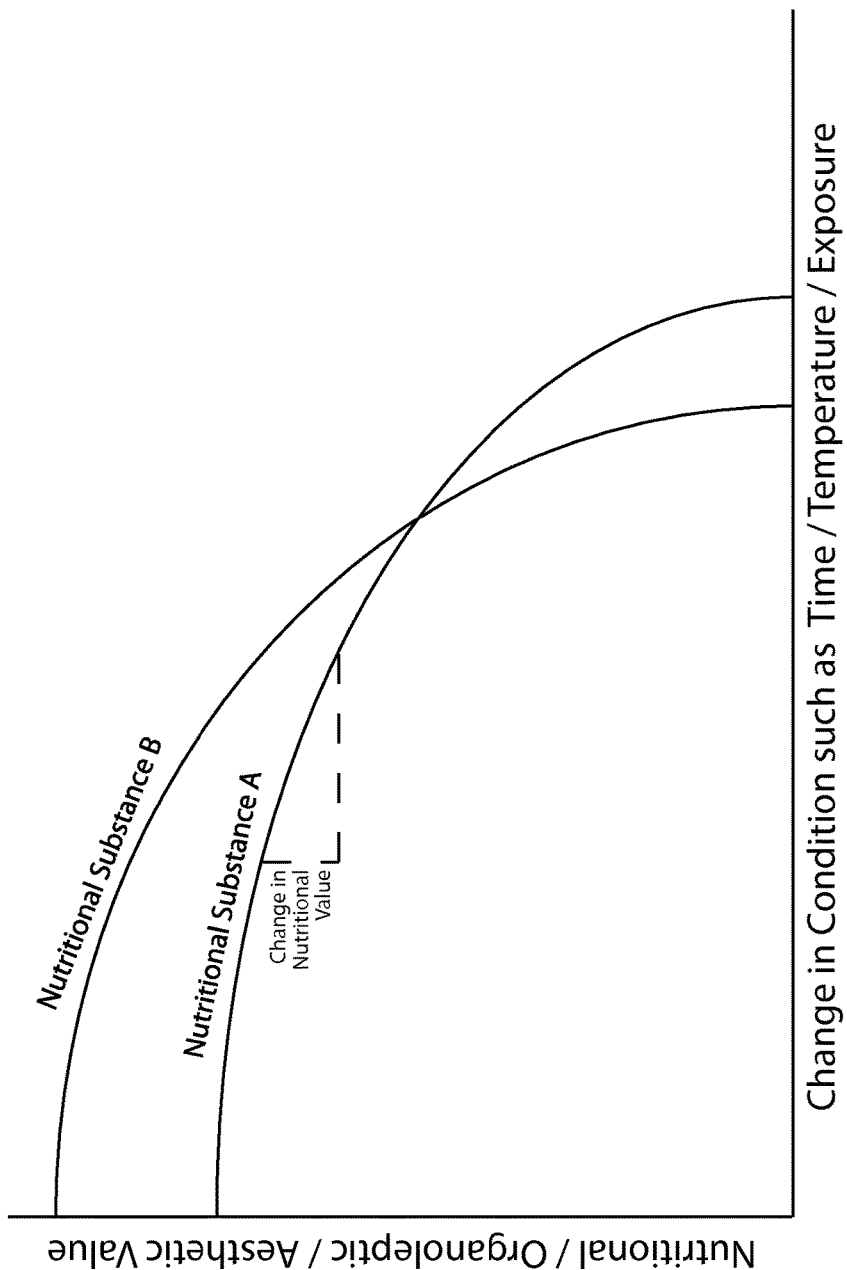
FIG. 2 shows a graph representing a value of a nutritional substance which changes according to a change of condition for the nutritional substance.

FIG. 2 is a graph showing the function of how a value of a nutritional substance varies over the change in a condition of the nutritional substance. Plotted on the vertical axis of this graph can be either the nutritional value, organoleptic value, or even the aesthetic value of a nutritional substance. Plotted on the horizontal axis can be the change in condition of nutritional substance over a variable such as time, temperature, location, and/or exposure to environmental conditions. This exposure to environmental conditions can include exposure to air, including oxygen, exposure to moisture, exposure to radiation such as heat or sunlight, or exposure to materials such as packaging. The function plotted as nutritional substance A could show the degradation of in the nutritional value of milk over time. Any point on this curve can be compared to another point to measure and/or describe the change in nutritional value. The plot of the degradation in nutritional value of nutritional substance B describes a nutritional substance which starts out with a higher nutritional value than nutritional substance A, but degrades over time more quickly than nutritional substance A.

If, in this example, where nutritional substance A and nutritional substance B are milk, this information regarding the nutritional substance degradation profile of each milk could be used by the consumer in the selection and/or consumption of the milk. If the consumer has this information at time zero when selecting a milk product for purchase, the consumer could consider when the consumer plans to consume the milk, whether that is on one occasion or multiple occasions. For example, if the consumer planned to consume the milk prior to the point when the curve represented by nutritional substance B crosses the curve represented by nutritional substance A, then the consumer should choose the milk represented by nutritional substance B because it has a higher nutritional value until it crosses the curve represented by nutritional substance A. However, if the consumer expects to consume at least some of the milk at a point in time after the time when the curve represented by nutritional substance B crosses the curve represented by nutritional substance A, then the consumer might choose to select the milk represented by the nutritional substance A, even though milk represented by nutritional substance A has a lower nutritional value than the milk represented by nutritional substance B at an earlier time. This change to a desired value in a nutritional substance over a change in the nutritional substance described in FIG. 2 can be measured and/or controlled throughout nutritional substance supply system 10 in FIG. 1.

In FIG. 1, Creation module 200 can dynamically encode nutritional substances to enable the tracking of nutritional, organoleptic, and/or aesthetic value of the nutritional substance. This dynamic encoding can replace and/or complement existing nutritional substance marking systems such as barcodes, labels, and/or ink markings. This dynamic encoding can be used to make nutritional substance information from creation module 200 available to information module 100 for use by preservation module 300, transformation module 400, conditioning module 500, and/or consumption module 600, which includes the ultimate consumer of the nutritional substance. One method of marking the nutritional substance by creation module 200 (or actually any other module in nutritional supply system 10) could include an electronic tagging system, such as the tagging system manufactured by Kovio of San Jose, Calif., USA. Such thin film chips can be used not only for tracking nutritional substances, by can include components to measure attributes of nutritional substances, and record and transmit such information. Such information may be readable by a reader including a satellite-based system. Such a satellite-based nutritional substance information tracking system could comprise a network of satellites with coverage of some or all the surface of the earth, so as to allow information module 100 real time, near real time updates about a particular nutritional substance.

Preservation module 300 includes packers and shippers of nutritional substances. The tracking of nutritional, organoleptic, and/or aesthetic values during the preservation period within preservation module 300 allows for dynamic expiration dates for nutritional substances. For example, expiration dates for dairy products are currently based generally only on time using assumptions regarding minimal conditions at which dairy products are maintained. This extrapolated expiration date is based on a worst-case scenario for when the product becomes unsafe to consume during the preservation period. In reality, the degradation of dairy products may be significantly less than this worst-case. If preservation module 300 could measure or derive the actual degradation information, the actual expiration date could be significantly later in time. This would allow the nutritional substance supply system to dispose of fewer products due to expiration dates. This ability to dynamically generate expiration dates for nutritional substances is of particular significance when nutritional substances contain few or no preservatives. Such products are highly valued throughout nutritional substance supply system 10, including consumers who are willing to pay a premium for nutritional substances with few or no preservatives.

By law, in many localities, food processors such as those in transformation module 400 are required to provide nutritional substance information regarding their products. Often, this information takes the form of a nutritional table applied to the packaging of the nutritional substance. Currently, the information in this nutritional table is based on averages or minimums for their typical product. Using the nutritional substance information from information module 100 provided by creation module 200, preservation module 300, and/or information from the transformation of the nutritional substance by transformation module 400, the food processor could include a nutritional table for the actual nutritional substance being supplied. The information in such a dynamically generated nutritional table could be used by conditioning module 500 in the preparation of the nutritional substance, and/or used by consumption module 600, so as to allow the ultimate consumer the ability to select the most desirable nutritional substance which meets their needs, and/or to track information regarding nutritional substances consumed.

The change in nutritional, organoleptic, and/or aesthetic value by conditioning module 500 is currently not tracked or provided to the consumer. However, using information provided by information module 100 from creation module 200, preservation module 300, transformation module 400, and/or information measured or generated by conditioning module 500, conditioning module 500 could provide consumer with the actual, and/or estimated change in nutritional, organoleptic, and/or aesthetic values of the nutritional substance. Such information regarding the change to nutritional, organoleptic and/or aesthetic value of the nutritional substance could be provided not only to the consumer, but could also be provided to information module 100 for use by creation module 200, preservation module 300, transformation module 400, so as to track, and possibly improve nutritional substances throughout the entire nutritional substance supply system 10.

The information regarding nutritional substances provided by information module 100 to consumption module 600 can replace or complement existing information sources such as recipe books, food databases like www.epicurious.com, and Epicurious apps. Through the use of specific information regarding a nutritional substance from information module 100, consumers can use consumption module 600 to select nutritional substances according to nutritional, organoleptic, and/or aesthetic values. This will allow consumers to make informed decisions regarding nutritional substance additives, preservatives, genetic modifications, origins, traceability, and other nutritional substance attributes. This information can be provided by consumption module 600 through personal computers, laptop computers, tablet computers, and/or smartphones. Software running on these devices can include dedicated computer programs, modules within general programs, and/or smartphone apps. An example of such a smartphone app regarding nutritional substances is the iOS ShopNoGMO from the Institute for Responsible Technology. This iPhone app allows consumers access to information regarding non-genetically modified organisms they may select. Additionally, consumption module 600 may provide information for the consumer to operate conditioning module 500 in such a manner as to preserve nutritional, organoleptic, and/or aesthetic value.

Through the use of nutritional substance information available from information module 100 nutritional substance supply system 10 can track nutritional, organoleptic, and/or aesthetic value. Using this information, nutritional substances travelling through nutritional substance supply system 10 can be dynamically valued and priced according to nutritional, organoleptic, and/or aesthetic values. For example, nutritional substances with longer expiration dates (longer shelf life) may be more highly valued than nutritional substances with shorter expiration dates. Additionally, nutritional substances with higher nutritional, organoleptic, and/or aesthetic values may be more highly valued, not just by the consumer, but also by each entity within nutritional substance supply system 10. This is because each entity will want to start with a nutritional substance with higher nutritional, organoleptic, and/or aesthetic value before it performs its function and passes the nutritional substance along to the next entity.

During the period of implementation of the present inventions, there will be nutritional substances being marketed which including the information, information-enabled nutritional substances, and nutritional substances which are not information enabled, dumb nutritional substances. Information-enabled nutritional substances would be available in virtual internet marketplaces, as well as traditional marketplaces. Because of information provided by information-enabled nutritional substances, entities within the nutritional substance supply system 10, including consumers, would be able to review and select information-enabled nutritional substances for purchase. It should be expected that, initially, the information-enabled nutritional substances would enjoy a higher market value and price than dumb nutritional substances. However, as information-enabled nutritional substances become more the norm, the cost savings from less waste due to degradation of information-enabled nutritional substances could lead to their price actually becoming less than dumb nutritional substances.

For example, the producer of a ready-to-eat dinner would prefer to use corn of a high nutritional, organoleptic, and/or aesthetic value in the production of its product, the ready-to-eat dinner, so as to produce a premium product of high nutritional, organoleptic, and/or aesthetic value. Depending upon the levels of the nutritional, organoleptic, and/or aesthetic values, the ready-to-eat dinner producer may be able to charge a premium price and/or differentiate its product from that of other producers. When selecting the corn to be used in the ready-to-eat dinner, the producer will seek corn of high nutritional, organoleptic, and/or aesthetic value from preservation module 300 that meets its requirements for nutritional, organoleptic, and/or aesthetic value. The packager/shipper of preservation module 300 would also be able to charge a premium for corn which has high nutritional, organoleptic, and/or aesthetic values. And finally, the packager/shipper of preservation module 300 will select corn of high nutritional, organoleptic, and/or aesthetic value from the grower of creation module 200, who will also be able to charge a premium for corn of high nutritional, organoleptic, and/or aesthetic values.

The nutritional, organoleptic, and/or aesthetic value for a nutritional substance tracked through nutritional substance supply system 10 through nutritional substance information from information module 100 can be preferably measured information. However, some or all such nutritional substance information may be derived through measurements of environmental conditions of the nutritional substance as it travelled through nutritional substance supply system 10. Additionally, some or all of nutritional substance information can be derived from data of other nutritional substances which have travelled through nutritional substance supply system 10. Finally, nutritional substance information can also be derived from laboratory experiments performed on other nutritional substances, which may approximate conditions and/or processes to which the actual nutritional substance has been exposed.

For example, laboratory experiments can be performed on bananas to determine effect on nutritional, organoleptic, and/or aesthetic value for a variety of environmental conditions bananas may be exposed to during packaging and shipment in preservation module 300. Using this experimental data, tables and/or algorithms could be developed which would predict the level of nutritional, organoleptic, and/or aesthetic values for a particular banana based upon information collected regarding the environmental conditions to which the banana was exposed during its time in preservation module 300. While the ultimate goal for nutritional substance supply system 10 would be the actual measurement of nutritional, organoleptic, and/or aesthetic values, use of derived nutritional, organoleptic, and/or aesthetic value from experimental information would allow more accurate tracking of nutritional, organoleptic, and/or aesthetic values while technology and systems are put in place to allow actual measurement.

Figure 3:
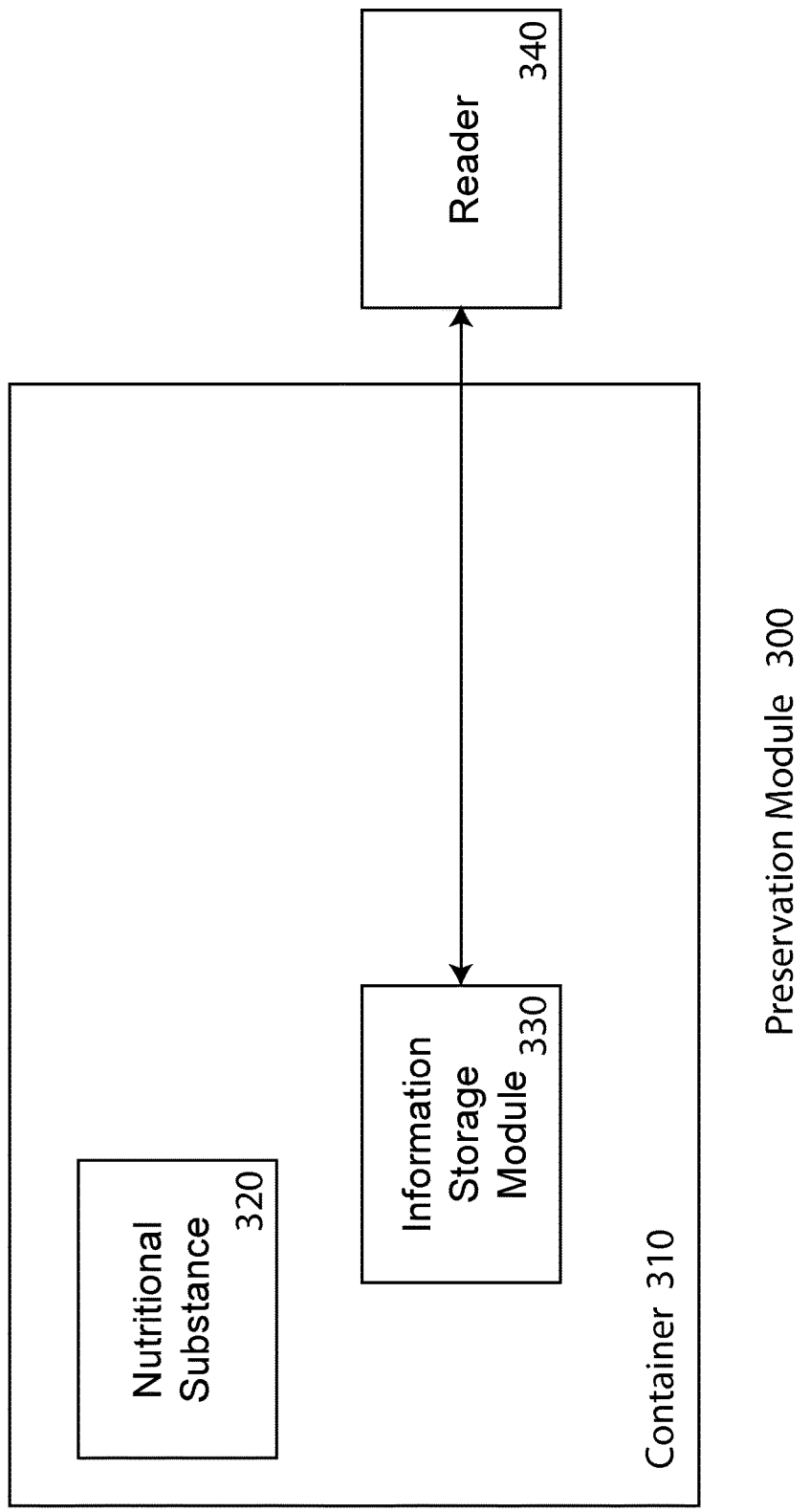
FIG. 3 shows a schematic functional block diagram of the preservation module 300 according to the present invention.

FIG. 3 shows an embodiment of the preservation module of the present invention. Preservation system 300 includes a container 310 which contains nutritional substance 320. Also included in container 310 is information storage module 330 which can be connected to an external reader 340. In this embodiment, information storage module 330 contains information regarding the nutritional substance 320. This information can include creation information from the creation of the nutritional substance 320. However, information in the information storage module 320 might include identification information, information regarding prior transformation of the nutritional substance 320, and other historic information. A shipper, or user, of container 310 can operatively connect to information storage module 330 using reader 340 to retrieve information stored therein.

In an alternate embodiment reader 340 can also write to information storage module 330. In this embodiment, information regarding the container and/or nutritional substance 320 can be modified or added to information storage module 330 by the user or shipper.

Figure 4:
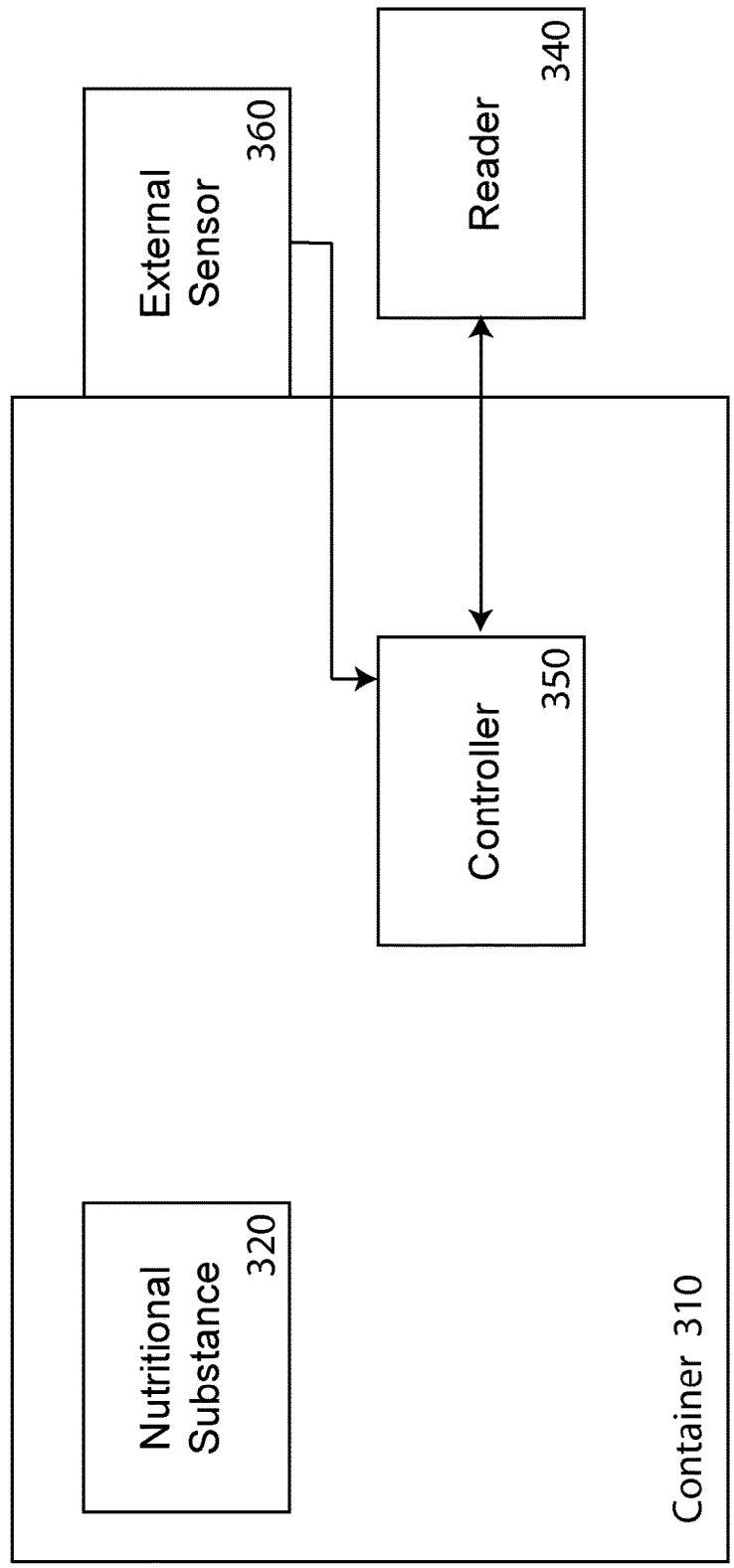
FIG. 4 shows a schematic functional block diagram of the preservation module 300 according to an alternate embodiment of the present invention.

FIG. 4 shows another embodiment of preservation system 300 wherein container 310 contains nutritional substance 320 as well as controller 350. Controller 350 is connected to external sensor 360 located either inside, on the surface of, or external to container 310 such that external sensor 360 can obtain information regarding the environment external to container 310. Controller 350 and exterior sensor 360 can take the form of electronic components such as a microcontroller and an electronic sensor. However, the controller-sensor combination may also be chemical or organic materials which perform the same function, such as a liquid crystal sensor/display.

When the shipper or user of container 310 desires information from external sensor 360 the shipper or user can use reader 340 to query the controller 350 as to the state of external sensor 360. In the electronic component embodiment, reader 340 could be a user interface device such as a computer which can be electronically connected to controller 350. In the liquid crystal sensor/display, the ready could be a human looking at the display.

In one embodiment, reader 340 can be directly connected to external sensor 360 to obtain the information from external sensor 360 without need of a controller 350. In another embodiment, external sensor 360 provides information to controller 350 which is presented as a visual display to the shipper or user. Finally, external sensor 360 could provide information directly to the user or shipper by visual means such as a temperature sensitive liquid crystal thermometer.

In an additional embodiment, controller 350 can modify the operation of container 310 so as modify the preservation capabilities of container 310. For example, if the exterior environment of container 310 would adversely affect the nutritional substance 320, container 310 could adjust the internal environment of container 310 to better preserve the nutritional substance. If nutritional substance needs to be kept within a certain temperature range to preserve its organoleptic and/or nutritional properties, and the external sensor 360 provide exterior temperature information to controller 350, controller 350 could modify container 310 so as to maintain nutritional substance 320 within the required temperature range.

Figure 5:
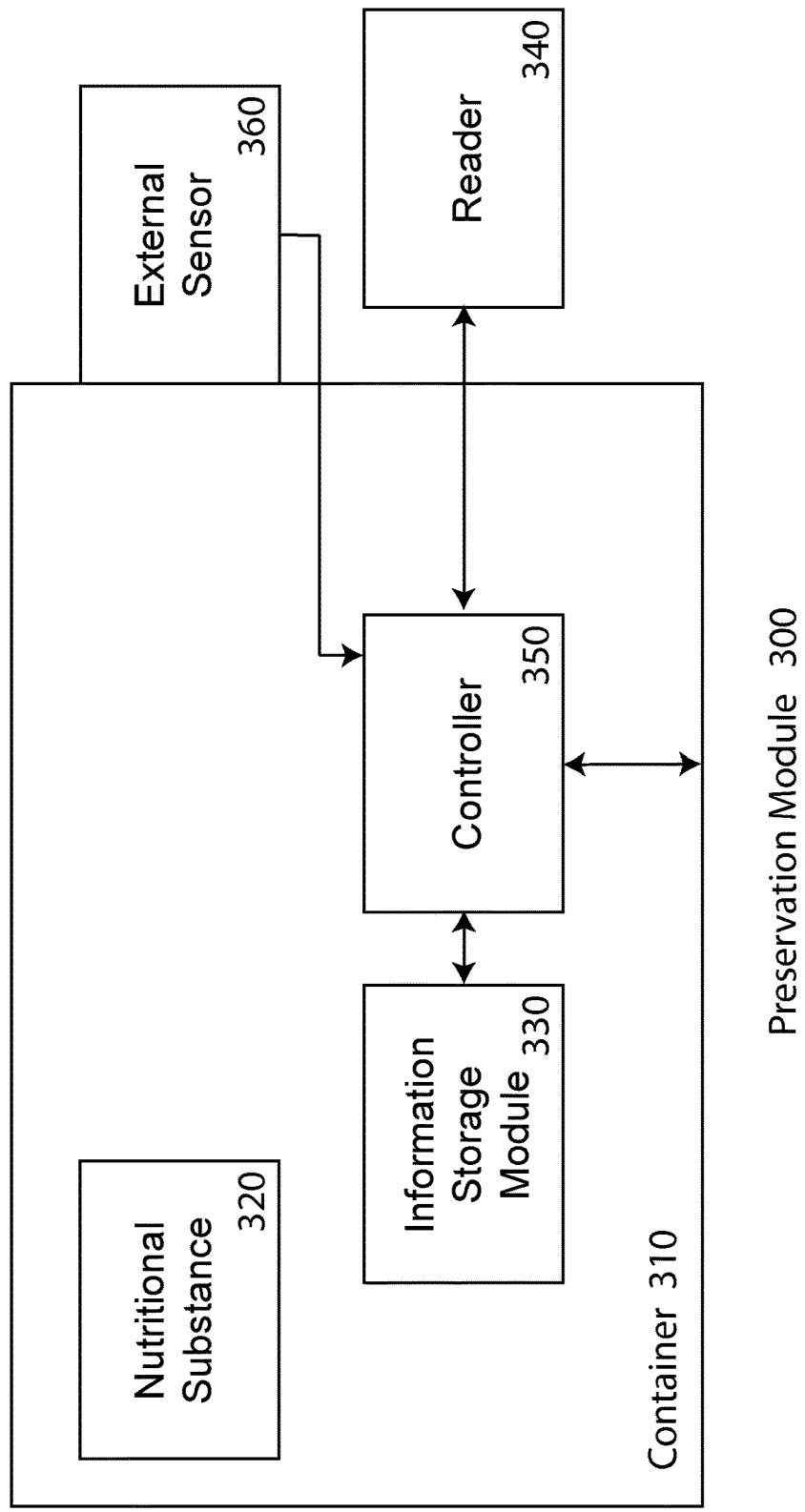
FIG. 5 shows a schematic functional block diagram of the preservation module 300 according to an alternate embodiment of the present invention.

In FIG. 5, preservation system 300 includes container 310 which contains nutritional substance 320, controller 350, and information storage module 330. External sensor 360 is positioned such that it can provide information on the exterior environment to container 310. Information from the external sensor and information storage module can be retrieved by connecting reader 340 to container 310.

In this embodiment, information regarding the external environment sensed by external sensor 360 and provided to controller 350 can be stored in information storage module 330. This storage of external environment can be used to record a history the external environment container 310 has been subjected to. This would allow the shipper or user of container 310 to understand the external environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the external conditions of the container.

Additionally, in this embodiment, information storage module 340 could contain other information regarding the nutritional substance, including creation information, identification information, and/or prior transformation information.

In an additional embodiment, controller 350 can modify the operation of container 310 so as modify the preservation capabilities of container 310. For example, if the exterior environment of container 310 would adversely affect the nutritional substance 320, container 310 could adjust the internal environment of container 310 to better preserve the nutritional substance. Controller 350 can analyze the historic information from external sensor 360, stored in information storage module 330 to determine any long-term exterior conditions environmental If nutritional substance needs to be kept within a certain temperature range to preserve its organoleptic and/or nutritional properties, and the external sensor 360 provide exterior temperature information to controller 350, controller 350 could modify container 310 so as to maintain nutritional substance 320 within the required temperature range.

Figure 6:
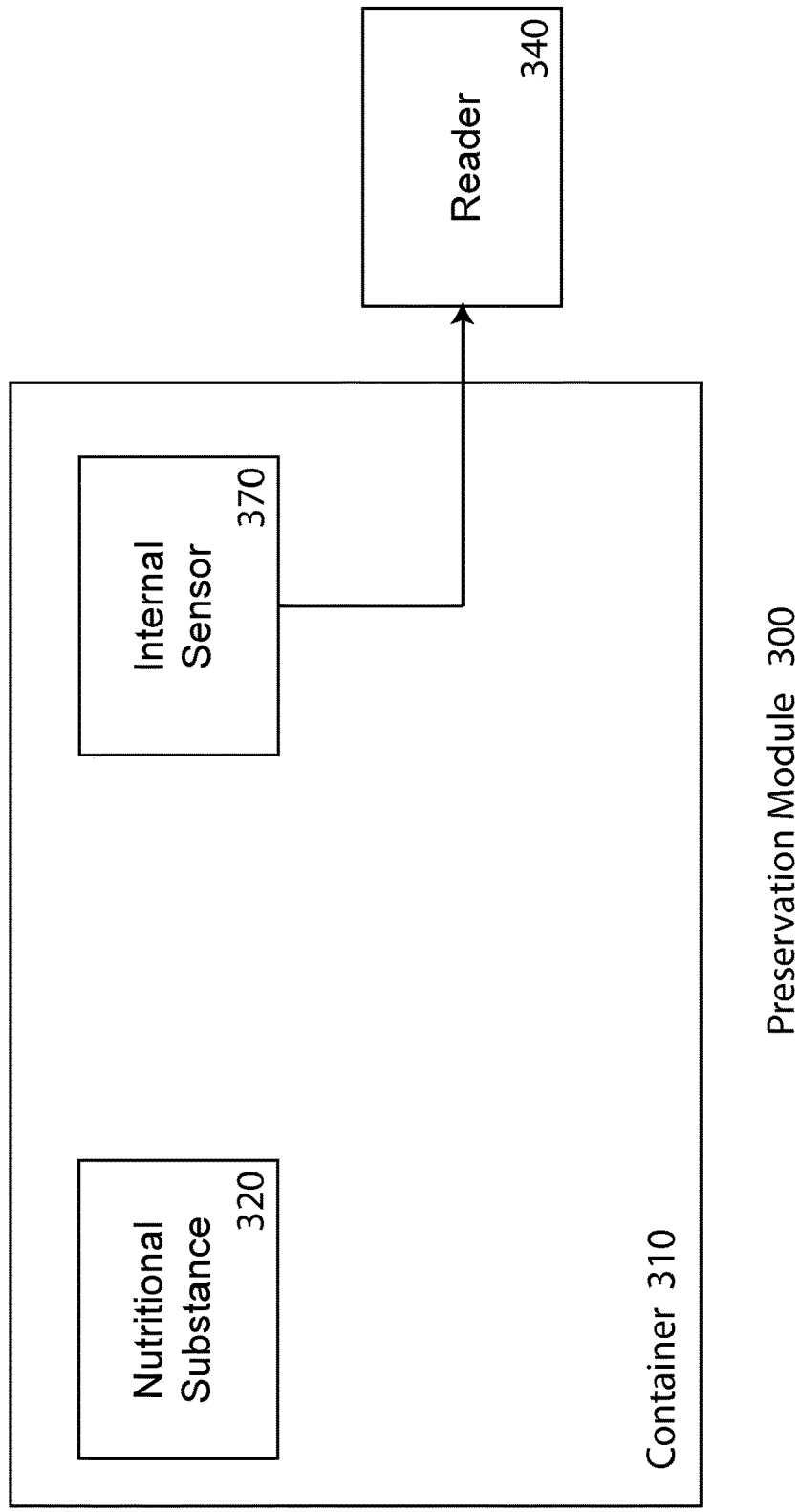
FIG. 6 shows a schematic functional block diagram of the preservation module 300 according to an alternate embodiment of the present invention.

FIG. 6 shows embodiment of preservation system 300 wherein container 310 contains nutritional substance 320 as well as internal sensor 370 located either inside, or on the surface of, container 310, such that internal sensor 370 can obtain information regarding the environment internal to container 310. Internal sensor 370 can be connected to reader 340 to obtain the interior conditions of container 310. Internal sensor 360 and reader 340 can take the form of electronic components such as an electronic sensor and electronic display. However, the controller-sensor combination may also be chemical or organic materials which perform the same function, such as a liquid crystal sensor/display.

Figure 7:
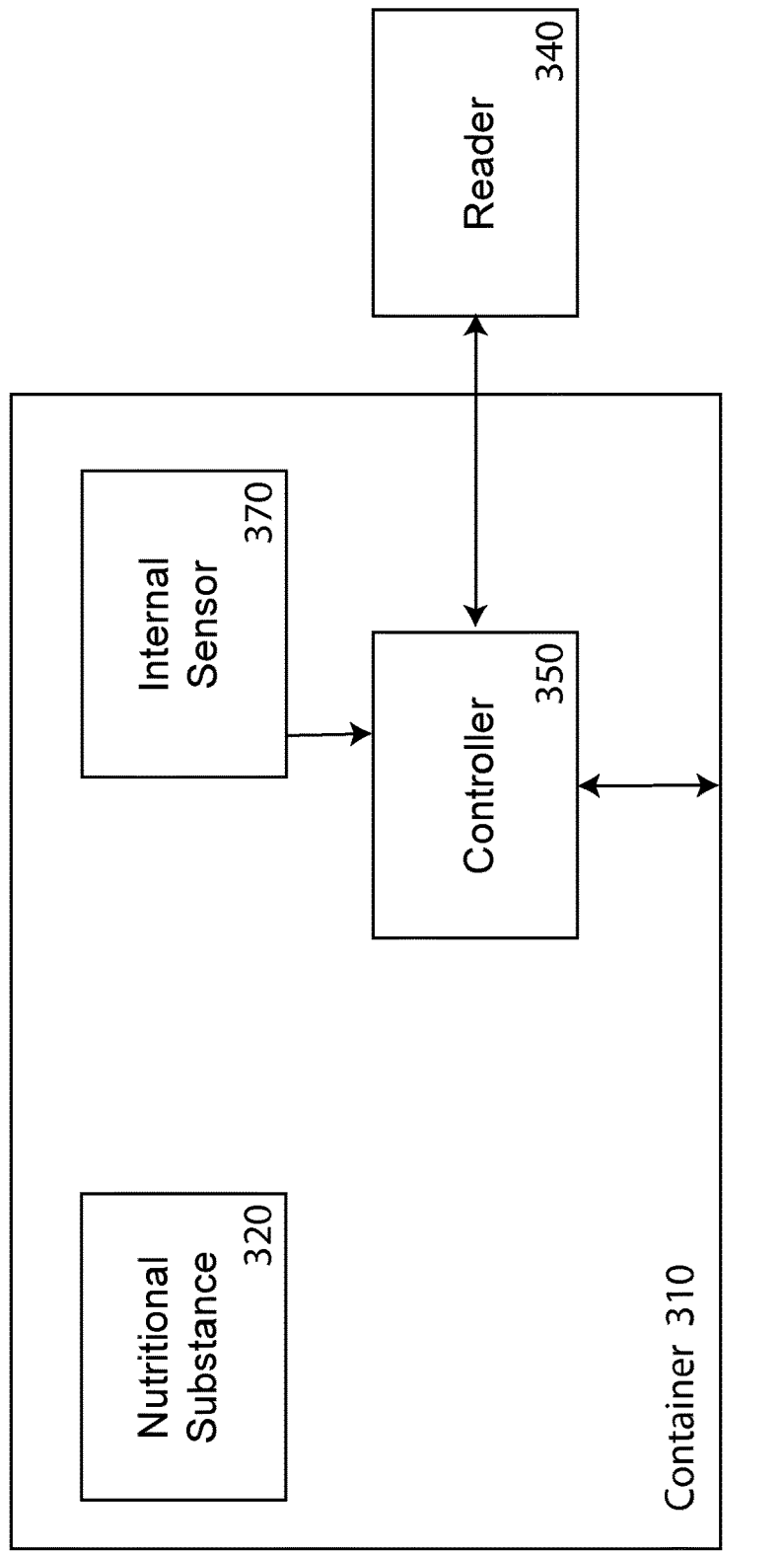
FIG. 7 shows a schematic functional block diagram of the preservation module 300 according to an alternate embodiment of the present invention.

FIG. 7 shows embodiment of preservation system 300 wherein container 310 contains nutritional substance 320 as well as controller 350. Controller 350 is connected to internal sensor 370 located either inside, or on the surface of, container 310, such that internal sensor 370 can obtain information regarding the environment internal to container 310. Controller 350 and internal sensor 360 can take the form of electronic components such as a micro-controller and an electronic sensor. However, the controller-sensor combination may also be chemical or organic materials which perform the same function, such as a liquid crystal sensor/display.

When the shipper or user of container 310 desires information from internal sensor 370 the shipper or user can use reader 340 to query internal sensor 370. In the electronic component embodiment, reader 340 could be a user interface device such as a computer which can be electronically connected to internal sensor 370.

In an additional embodiment, controller 350 can modify the operation of container 310 so as modify the preservation capabilities of container 310. For example, if the interior environment of container 310 would adversely affect the nutritional substance 320, container 310 could adjust the internal environment of container 310 to better preserve the nutritional substance. If nutritional substance needs to be kept within a certain temperature range to preserve its organoleptic and/or nutritional properties, and the internal sensor 370 provide internal temperature information to controller 350, controller 350 could modify container 310 so as to maintain nutritional substance 320 within the required temperature range.

Figure 8:
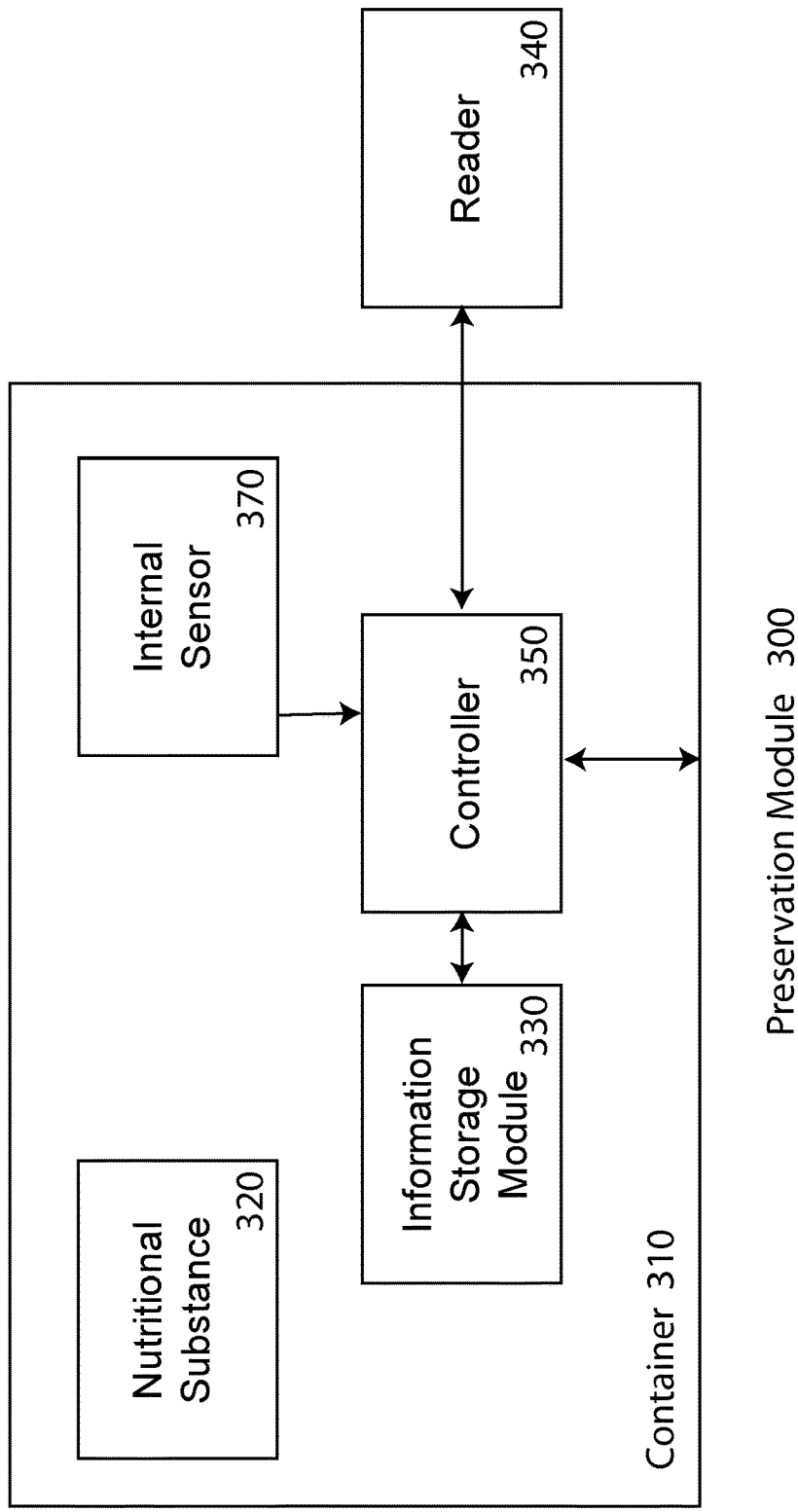
FIG. 8 shows a schematic functional block diagram of the preservation module 300 according to an alternate embodiment of the present invention.

In FIG. 8, preservation system 300 includes container 310 which contains nutritional substance 320, controller 350, and information storage module 330. Internal sensor 370 is positioned such that it can provide information on the internal environment to container 310. Information from the internal sensor and information storage module can be retrieved by connecting reader 340 to container 310.

In this embodiment, information regarding the internal environment sensed by internal sensor 370 and provided to controller 350 can be stored in information storage module 330. This storage of internal environment can be used to record a history the internal environment container 310 has been subjected to. This would allow the shipper or user of container 310 to understand the internal environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the internal conditions of the container.

Additionally, in this embodiment, information storage module 340 could contain other information regarding the nutritional substance, including creation information, identification information, and/or prior transformation information.

In an additional embodiment, controller 350 can modify the operation of container 310 so as modify the preservation capabilities of container 310. For example, if the internal environment of container 310 would adversely affect the nutritional substance 320, container 310 could adjust the internal environment of container 310 to better preserve the nutritional substance. Controller 350 can analyze the historic information from internal sensor 370, stored in information storage module 330 to determine any long-term internal conditions environmental If nutritional substance needs to be kept within a certain temperature range to preserve its organoleptic and/or nutritional properties, and the internal sensor 370 provide internal temperature information to controller 350, controller 350 could modify container 310 so as to maintain nutritional substance 320 within the required temperature range.

Information in the information storage module 320 might include identification information, information regarding prior transformation of the nutritional substance 320, and other historic information. A shipper, or user, of container 310 can operatively connect to information storage module 330 using reader 340 to retrieve information stored therein. In an alternate embodiment reader 340 can also write to information storage module 330. In this embodiment, information regarding the container and/or nutritional substance 320 can be modified or added to information storage module 330 by the user or shipper.

Figure 9:
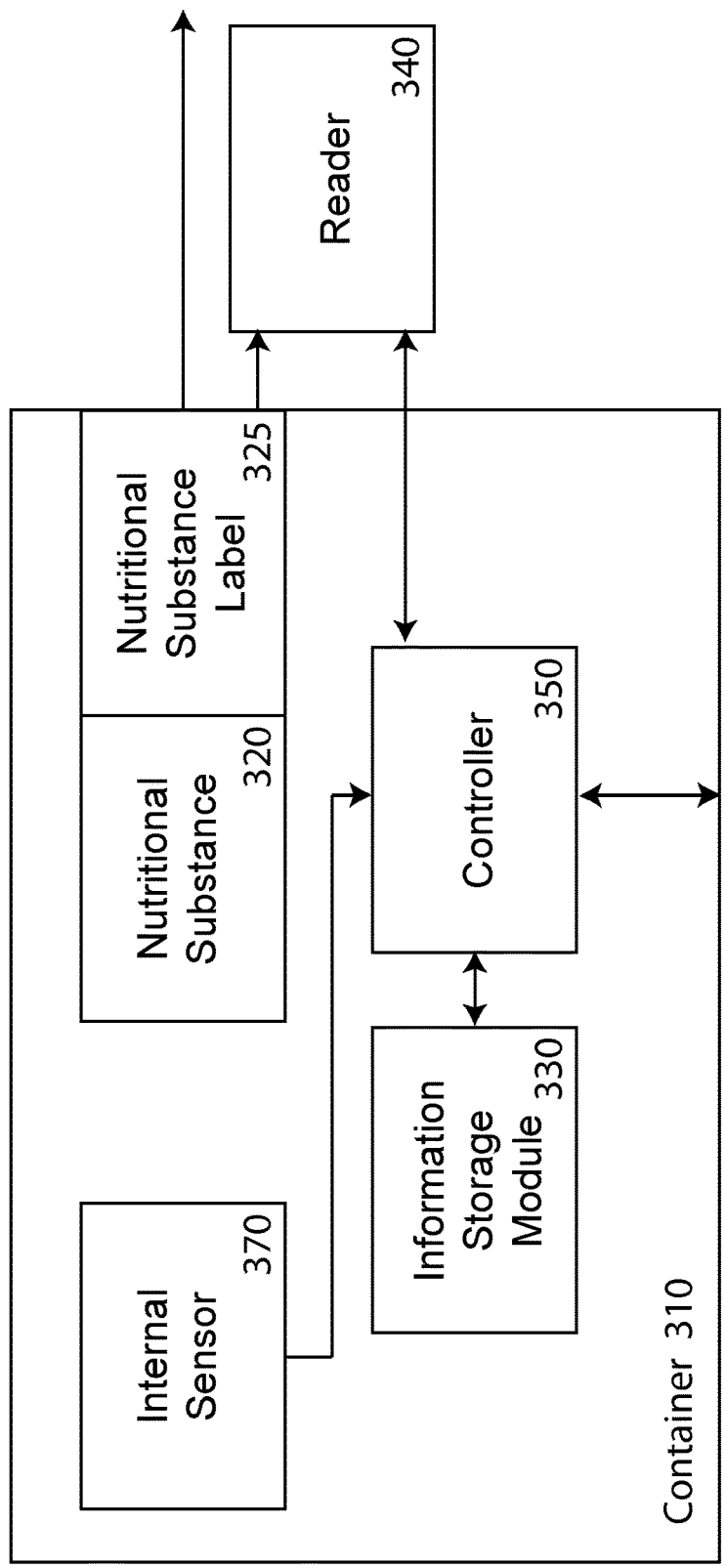
FIG. 9 shows a schematic functional block diagram of the preservation module 300 according to an alternate embodiment of the present invention.

FIG. 9 shows an alternate embodiment of the present invention. Preservation system 300 includes container 310 which contains nutritional substance 320, nutritional substance label 325, controller 350, and information storage module 330. Internal sensor 370 is positioned such that it can provide information on the internal environment to container 310. Information from the internal sensor and information storage module can be retrieved by connecting reader 340 to container 310. Nutritional substance label 325 is attached to nutritional substance 320 so as to sense, measure, and/or indicate the current state of nutritional substance 320. Nutritional substance label 325 can be read by reader 340. Nutritional substance label 325 could be a material/chemical tag that, through a physical reaction with the surface of nutritional substance 320, provides information regarding the organoleptic state of the nutritional substance, including where nutritional substance 320 is in its life cycle. As an example, this label/tag can could change color as a fruit, cheese or wine matures across time. It could also indicate if it detects traces of pesticides, hormones, allergens, harmful or dangerous bacteria, or any other substances.

In this embodiment, information regarding the internal environment sensed by internal sensor 370 and provided to controller 350 can be stored in information storage module 330. This storage of internal environment can be used to record a history the internal environment container 310 has been subjected to. This would allow the shipper or user of container 310 to understand the internal environment the container has been subjected to during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the internal conditions of the container.

Additionally, in this embodiment, information storage module 340 could contain other information regarding the nutritional substance, including creation information, identification information, and/or prior transformation information.

In an additional embodiment, controller 350 can modify the operation of container 310 so as modify the preservation capabilities of container 310. For example, if the internal environment of container 310 would adversely affect the nutritional substance 320, container 310 could adjust the internal environment of container 310 to better preserve the nutritional substance. Controller 350 can analyze the historic information from internal sensor 370, stored in information storage module 330 to determine any long-term internal conditions environmental If nutritional substance needs to be kept within a certain temperature range to preserve its organoleptic and/or nutritional properties, and the internal sensor 370 provide internal temperature information to controller 350, controller 350 could modify container 310 so as to maintain nutritional substance 320 within the required temperature range.

Information in the information storage module 320 might include identification information, information regarding prior transformation of the nutritional substance 320, and other historic information. A shipper, or user, of container 310 can operatively connect to information storage module 330 using reader 340 to retrieve information stored therein. Additionally, such a shipper, or user, of container 310 can obtain information from nutritional substance label 325, either through direct observation or through reader 340. In an alternate embodiment reader 340 can also write to information storage module 330. In this embodiment, information regarding the container and/or nutritional substance 320 can be modified or added to information storage module 330 by the user or shipper.

Figure 10:
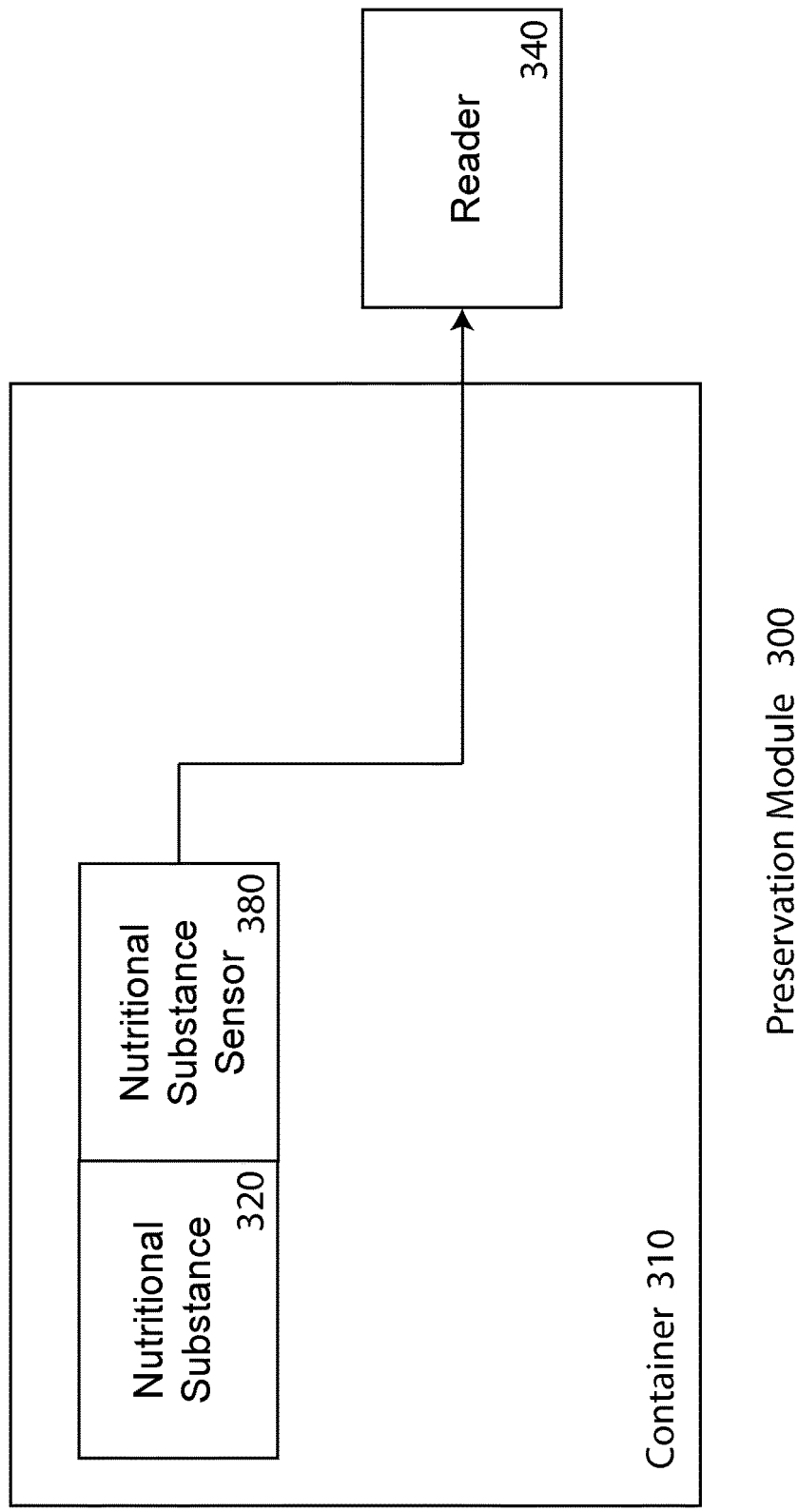
FIG. 10 shows a schematic functional block diagram of the preservation module 300 according to an alternate embodiment of the present invention.

FIG. 10 shows embodiment of preservation system 300 wherein container 310 contains nutritional substance 320 as well as nutritional substance sensor 380 in contact with nutritional substance 320, such that nutritional substance sensor 380 can obtain information regarding the nutritional substance 320 in container 310. Nutritional substance sensor 380 can be connected to reader 340 to obtain the nutritional substance 320 condition. Nutritional substance sensor 380 and reader 340 can take the form of electronic components such as an electronic sensor and electronic display. However, the controller-sensor combination may also be chemical or organic materials which perform the same function, such as a liquid crystal sensor/display.

Figure 11:
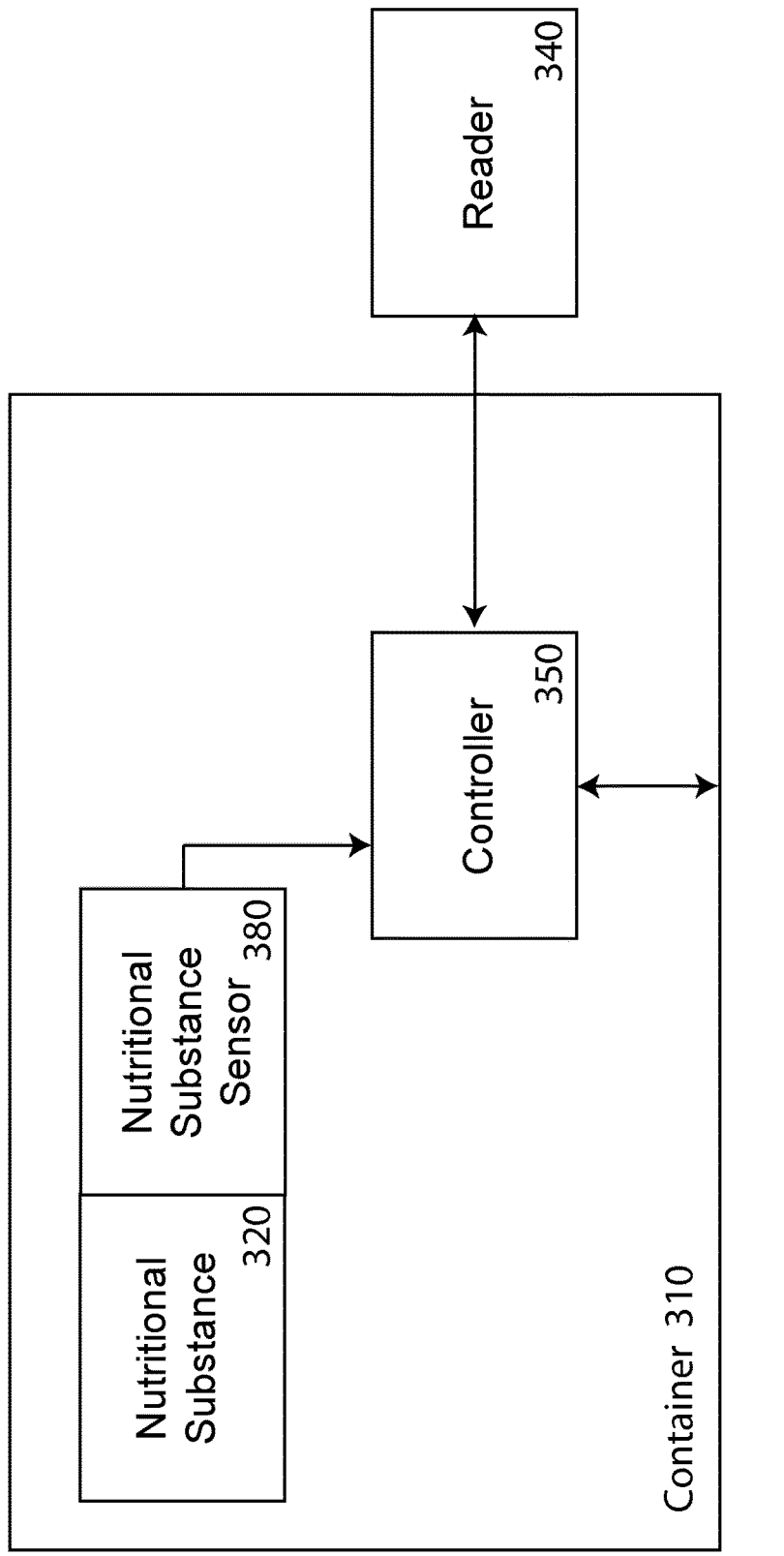
FIG. 11 shows a schematic functional block diagram of the preservation module 300 according to an alternate embodiment of the present invention.

FIG. 11 shows embodiment of preservation system 300 wherein container 310 contains nutritional substance 320 as well as controller 350. Controller 350 is connected to nutritional substance sensor 380. Controller 350 and nutritional substance sensor 380 can take the form of electronic components such as a micro-controller and an electronic sensor. However, the controller-sensor combination may also be chemical or organic materials which perform the same function, such as a liquid crystal sensor/display.

When the shipper or user of container 310 desires information from nutritional substance sensor-380 the shipper or user can use reader 340 to query nutritional substance sensor 380. In the electronic component embodiment, reader 340 could be a user interface device such as a computer which can be electronically connected to nutritional substance sensor 380.

In an additional embodiment, controller 350 can modify the operation of container 310 so as modify the preservation capabilities of container 310. For example, if the interior environment of container 310 is adversely affecting the nutritional substance 320, container 310 could adjust the nutritional substance environment of container 310 to better preserve the nutritional substance. If nutritional substance needs to be kept within a certain temperature range to preserve its organoleptic and/or nutritional properties, and the nutritional substance sensor 380 provide nutritional substance temperature information to controller 350, controller 350 could modify container 310 so as to maintain nutritional substance 320 within the required temperature range.

Figure 12:
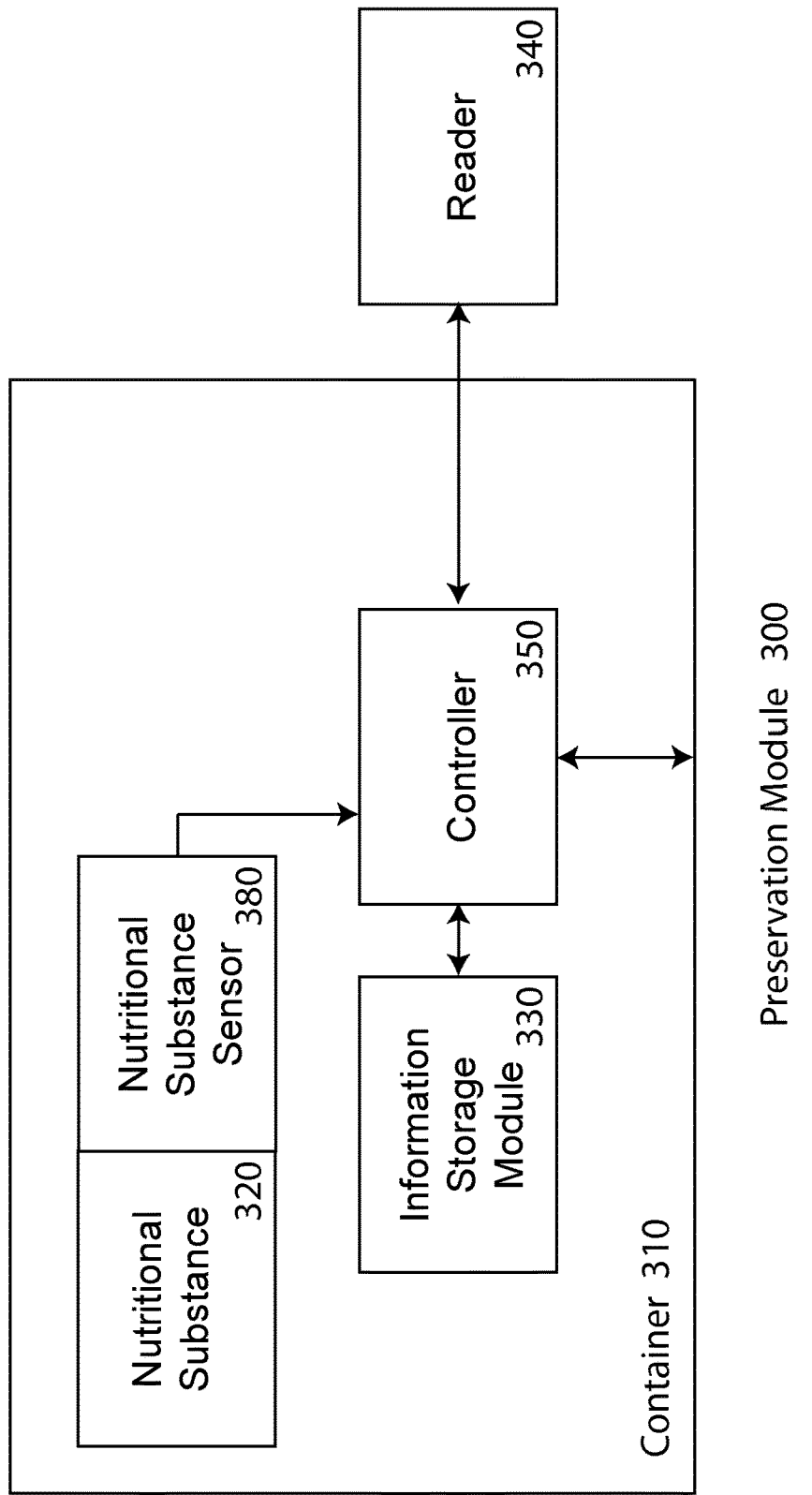
FIG. 12 shows a schematic functional block diagram of the preservation module 300 according to an alternate embodiment of the present invention.

In FIG. 12, preservation system 300 includes container 310 which contains nutritional substance 320, controller 350, and information storage module 330. Nutritional substance sensor 380 is positioned such that it can provide information on the nutritional substance in container 310. Information from the nutritional substance sensor 380 and information storage module can be retrieved by connecting reader 340 to controller 350.

In this embodiment, information regarding the nutritional substance sensed by nutritional substance sensor 380, and provided to controller 350, can be stored in information storage module 330. This storage of nutritional substance environment can be used to record a history the nutritional substance. This would allow the shipper or user of container 310 to understand the nutritional substance during the time it has preserved the nutritional substance. Such information can be used to determine if the nutritional substance is no longer safe for consumption or has been degraded such that the nutritional substance is no longer in an optimal state. Additionally, the user of the nutritional substance could modify its transformation, conditioning, or consumption according to any changes that may have occurred because of the conditions of the container.

Additionally, in this embodiment, information storage module 330 could contain other information regarding the nutritional substance, including creation information, identification information, and/or prior transformation information.

In an additional embodiment, controller 350 can modify the operation of container 310 so as modify the preservation capabilities of container 310. For example, if the nutritional substance 320 is being adversely affected, controller 350 could adjust the container 310 to better preserve the nutritional substance. Controller 350 can analyze the historic information from nutritional substance sensor 380 stored in information storage module 330 to determine any long-term nutritional substance conditions that need to be changed, If nutritional substance needs to be kept within a certain temperature range to preserve its organoleptic and/or nutritional properties, and the nutritional substance sensor 380 provide nutritional substance temperature information to controller 350, controller 350 could modify container 310 so as to maintain nutritional substance 320 within the required temperature range.

Information in the information storage module 320 might include identification information, information regarding prior transformation of the nutritional substance 320, and other historic information. A shipper, or user, of container 310 can operatively connect to information storage module 330 using reader 340 to retrieve information stored therein. In an alternate embodiment reader 340 can also write to information storage module 330. In this embodiment, information regarding the container and/or nutritional substance 320 can be modified or added to information storage module 330 by the user or shipper.

Figure 13:
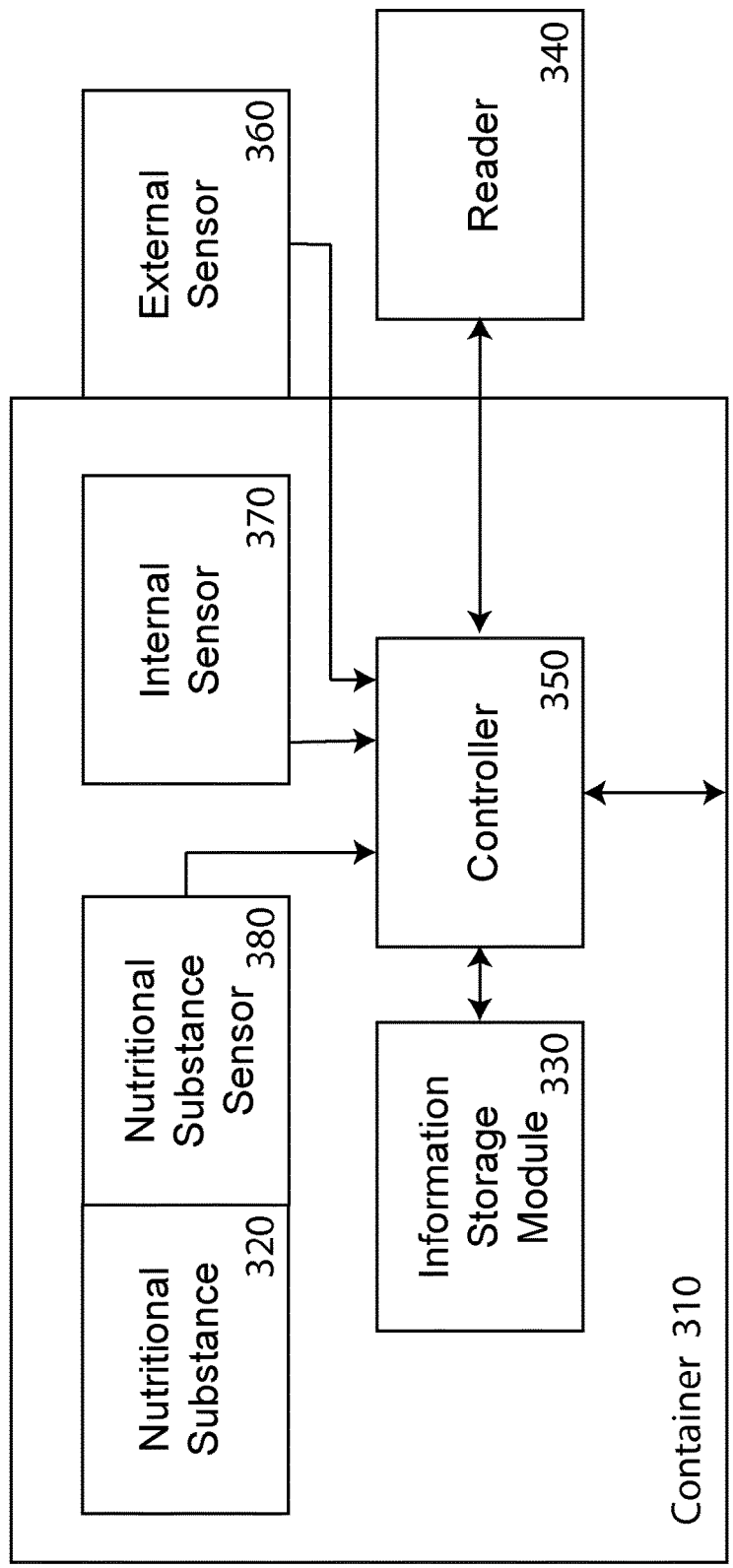
FIG. 13 shows a schematic functional block diagram of the preservation module 300 according to an alternate embodiment of the present invention.

FIG. 13 shows the preferred embodiment of preservation module 300. Within container 310 is nutritional substance 320, nutritional substance sensor 380, internal sensor 370, information storage module 340, and controller 350. External sensor 360 is located outside or on the surface of container 310. In operation, controller 350 receives information from nutritional substance sensor 380, internal sensor 370, and external sensor 360. Additionally, controller 350 can store the information received from the three sensors in information storage module 330. Controller 350 can retrieve such stored information and transmit it to reader 340. Reader 340 can also transmit instructions to controller 350.

Controller 350 is operably connected to container 310 so as to use the information obtained from the sensors and/or information stored in the information storage module to modify the operation of container 310 to affect the state of nutritional substance 320. Additionally, storage module 330 could contain information regarding nutritional substance 320 as to its identity, creation information and/or prior transformation information. This historic information could also be used in modifying the operation of container 310 in its preservation of nutritional substance 320.

As an example, nutritional substance 320 could be bananas being shipped to a distribution warehouse. Bananas are in container 310 which is capable of controlling its internal temperature, humidity, and the level of certain gasses within the container. Creation information as to the bananas is placed in information storage module 330 prior to shipment. During shipment, external sensor 360 measures the temperature and humidity outside container 310. This information is stored by controller 350 in information storage module 330. Controller 350 also receives information on the internal environment within container 310 from internal sensor 370 and stores this information in information storage module 330. This information includes the internal temperature, humidity, and certain gas levels within container 310. Finally, nutritional substance sensor 380, which is attached to the surface of the bananas, provides information as to the state of the bananas to controller 350. This information could include surface temperature, surface humidity, gasses being emitted, and surface chemicals. At any time during its shipment and delivery to the distribution warehouse, reader 340 can be used to retrieve both current information and historic information stored within information storage module 330.

During shipment, container 310 modifies its internal conditions according to instructions provided by controller 350. Controller 350 contains instructions as to how to preserve, and possibly ripen, the bananas using information stored in information storage module 330 about the creation of the bananas, as well as historical information received from the three sensors, as well as current information being received from the three sensors. In this manner, preservation module 300 can preserve and optimize organoleptic and nutritional attributes of the bananas while they are being shipped and stored.

It will be understood that subsets of the embodiment described herein can operate to achieve the goals stated herein. In one embodiment, nutritional substance sensor 380, internal sensor 370, external sensor 360, information storage module 330, controller 350, reader 340, and parts of container 310 are each electrical or electromechanical devices which perform each of the indicated functions. However, it is possible for some or all of these functions to be done using chemical and/or organic compounds. For example, a specifically designed plastic wrap for bananas can sense the exterior conditions of the package, the interior conditions of the package, and control gas flow through its surface so as to preserve and ripen the bananas.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize. While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. § 112, sixth paragraph, other aspects may likewise be embodied as a means-plus-function claim, or in other forms, such as being embodied in a computer-readable medium. Any claims intended to be treated under 35 U.S.C. § 112, ¶ 6 will begin with the words "means for." Accordingly, the applicant reserves the right to add additional claims after filing the application to pursue such additional claim forms for other aspects of the invention.

The invention claimed is:

1. A nutritional substance tracking system for tracking the nutritional, organoleptic and/or aesthetic values of a nutritional substance at creation of said nutritional substance, comprising:
   adaptive preserver for adaptively preserving a nutritional substance, wherein the adaptive preserver and the nutritional substance are inside a container;
   a sensor embedded in a plastic wrap containing the nutritional substance for sensing an attribute of the nutritional substance;
   attribute storage for storing said attribute of the nutritional substance;
   wherein the adaptive preserver preserves said nutritional substance in response to the sensed attribute of the nutritional substance so as to minimize degradation of said nutritional, organoleptic and/or aesthetic values of the nutritional substance by modifying the internal temperature within the container.

2. The preservation system of claim 1, wherein said attribute storage comprises a computer.

3. The preservation system of claim 1, wherein said attribute storage comprises a database.

\* \* \* \* \*